(12) United States Patent
Bobyn et al.

(10) Patent No.: US 8,309,536 B2
(45) Date of Patent: *Nov. 13, 2012

(54) IMPLANT IMPROVING LOCAL BONE FORMATION

(76) Inventors: John Dennis Bobyn, Westmount (CA); Michael Tanzer, Hampstead (CA)

(*) Notice: Subject to any disclaimer, the term of this patent is extended or adjusted under 35 U.S.C. 154(b) by 0 days.

This patent is subject to a terminal disclaimer.

(21) Appl. No.: 12/889,932

(22) Filed: Sep. 24, 2010

(65) Prior Publication Data

US 2011/0014265 A1 Jan. 20, 2011

Related U.S. Application Data

(63) Continuation of application No. 11/061,745, filed on Feb. 22, 2005.

(51) Int. Cl.
*A01N 57/00* (2006.01)

(52) U.S. Cl. ....... 514/102; 514/183; 514/91; 623/11.11; 623/13.12; 623/16.11; 623/17.11; 623/20.11

(58) Field of Classification Search .................. None
See application file for complete search history.

(56) References Cited

U.S. PATENT DOCUMENTS

| | | | |
|---|---|---|---|
| 4,330,514 A | 5/1982 | Nagai et al. |
| 4,795,475 A | 1/1989 | Walker |
| 4,939,130 A | 7/1990 | Jaeggi et al. |
| 5,118,667 A | 6/1992 | Adams et al. |
| 5,246,530 A | 9/1993 | Bugle et al. |
| 5,279,831 A | 1/1994 | Constantz et al. |
| 5,403,829 A | 4/1995 | Lehtinen et al. |
| 5,488,041 A | 1/1996 | Barbier et al. |
| 5,646,134 A | 7/1997 | Yates |
| 5,652,227 A | 7/1997 | Teronen et al. |
| 5,733,564 A | 3/1998 | Lehtinen |
| 5,876,454 A | 3/1999 | Nanci et al. |
| 5,891,863 A | 4/1999 | Yates |
| 5,947,893 A | 9/1999 | Agrawal et al. |
| 5,965,547 A | 10/1999 | Goodship et al. |
| 5,972,913 A | 10/1999 | Yates |
| 6,117,856 A | 9/2000 | Binderman et al. |
| 6,190,412 B1 | 2/2001 | Lee et al. |
| 6,203,573 B1 | 3/2001 | Walter et al. |
| 6,214,049 B1 | 4/2001 | Gayer et al. |
| 6,255,288 B1 | 7/2001 | Goodship et al. |
| 6,399,592 B1 | 6/2002 | Whiteford |
| 6,416,737 B1 | 7/2002 | Manolagas et al. |
| 6,455,514 B2 | 9/2002 | Du Mesnil et al. |
| 6,461,385 B1 | 10/2002 | Gayer et al. |
| 6,508,838 B2 | 1/2003 | Lee et al. |
| 6,558,702 B2 | 5/2003 | Dasch et al. |
| 6,572,874 B1 | 6/2003 | Harrison et al. |
| 6,677,320 B2 | 1/2004 | Diederich et al. |
| 6,680,307 B1 | 1/2004 | Bauss et al. |
| 6,696,429 B2 | 2/2004 | Du Mesnil et al. |
| 7,074,426 B2 | 7/2006 | Kochinke |
| 7,074,432 B2 | 7/2006 | Dasch et al. |
| 7,090,496 B2 | 8/2006 | Descouts et al. |
| 7,332,603 B2 | 2/2008 | De Ferra et al. |
| 7,361,761 B2 | 4/2008 | Senthilkumar et al. |
| 7,598,246 B2 | 10/2009 | Dixon et al. |
| 2001/0006960 A1 | 7/2001 | Du Mesnil et al. |
| 2001/0016203 A1 | 8/2001 | Lee et al. |
| 2002/0019351 A1 | 2/2002 | Ke et al. |
| 2002/0107228 A1 | 8/2002 | Binderman et al. |
| 2002/0151876 A1 | 10/2002 | Chan |
| 2002/0156529 A1 | 10/2002 | Li et al. |
| 2003/0004100 A1 | 1/2003 | Dasch et al. |
| 2003/0023308 A1 | 1/2003 | Leroux et al. |
| 2003/0027151 A1 | 2/2003 | Warman et al. |
| 2003/0032627 A1 | 2/2003 | Mesnil et al. |
| 2003/0036799 A1 | 2/2003 | Lee et al. |
| 2003/0044408 A1 | 3/2003 | Levy et al. |
| 2003/0055511 A1 | 3/2003 | Schryver et al. |
| 2003/0064965 A1 | 4/2003 | Richter |

(Continued)

FOREIGN PATENT DOCUMENTS

| | | |
|---|---|---|
| CA | 2508085 | 8/2006 |
| EP | 0637254 | 10/2002 |
| EP | 1343546 | 4/2006 |
| EP | 1351722 | 7/2006 |
| EP | 1698357 | 9/2006 |

(Continued)

OTHER PUBLICATIONS

Peter, et al.., Orthopaedic Implant as Drug Delivery System:Numerical, In vitro and in vivo approaches, 2004, 7$^{th}$ World Biomaterials Congress, p. 1174.*

Geesink, R. G. T., et al., Chemical Implant Fixation Using Hydroxyl-Apatite Coatings: The Development of a Human Total Hip Prosthesis for Chemical Fixation to Bone Using Hydroxyl-Apatite Coatings on Titanium Substrates, Clinical Orthopaedics and Related Research, 225:147-170, 1987.

Geesink, R., Hydroxyapatite-Coated Total Hip Prostheses, Clinical Orthopaedics and Related Research; 225:147-170, 1990.

(Continued)

*Primary Examiner* — Lezah Roberts
*Assistant Examiner* — Nannette Holloman
(74) *Attorney, Agent, or Firm* — McCarter & English, LLP

(57) ABSTRACT

A bone implant comprises an active agent on at least a portion thereof. The active agent is locally deliverable to bone proximate the implant in at least a two-phased release scheme. A first phase rapidly releases a first quantity of the active agent, and at least a second phase gradually releases a second quantity of the active agent, whereby bone formation stimulated by the active agent is modulated. In one embodiment, a porous implant comprises a porous portion coated with a calcium phosphate compound and which is contacted with a bisphosphonate compound to form a bisphosphonate layer chemically bound to the calcium phosphate at the surface of the porous portion and to form bisphosphonate molecules being non-chemically attached inside the pores of the porous portion. The non-chemically attached bisphosphonate molecules are released in the subject at a rate greater than that of the chemically bound bisphosphonate layer.

41 Claims, 8 Drawing Sheets

U.S. PATENT DOCUMENTS

| | | | |
|---|---|---|---|
| 2003/0100947 A1 | 5/2003 | Nadler et al. |
| 2003/0175340 A1 | 9/2003 | McCallister et al. |
| 2003/0176397 A1 | 9/2003 | Lichtenberger |
| 2003/0180262 A1 | 9/2003 | Wironen et al. |
| 2003/0181421 A1 | 9/2003 | Horowitz et al. |
| 2003/0196274 A1 | 10/2003 | Levy et al. |
| 2003/0220297 A1 | 11/2003 | Berstein et al. |
| 2004/0005345 A1 | 1/2004 | Pauletti et al. |
| 2004/0014726 A1 | 1/2004 | Osterman et al. |
| 2004/0023048 A1 | 2/2004 | Schwartz et al. |
| 2004/0049287 A1 | 3/2004 | Descouts et al. |
| 2004/0054422 A1 | 3/2004 | Descouts et al. |
| 2004/0073024 A1 | 4/2004 | Metcalf, III et al. |
| 2004/0092698 A1 | 5/2004 | Alferiev et al. |
| 2004/0097468 A1 | 5/2004 | Wimalawansa |
| 2004/0097469 A1 | 5/2004 | Little et al. |
| 2004/0102598 A1 | 5/2004 | Alferiev et al. |
| 2004/0110726 A1 | 6/2004 | Du Mesnil et al. |
| 2004/0116375 A1 | 6/2004 | Abraham |
| 2004/0127735 A1 | 7/2004 | Hostetler et al. |
| 2004/0147486 A1 | 7/2004 | Szymanski et al. |
| 2004/0147488 A1 | 7/2004 | Dasch et al. |
| 2004/0157798 A1 | 8/2004 | Little |
| 2004/0158098 A1 | 8/2004 | Finkelstein et al. |
| 2004/0158329 A1 | 8/2004 | Link |
| 2004/0186301 A1 | 9/2004 | Gravel et al. |
| 2004/0186576 A1 | 9/2004 | Biscup et al. |
| 2004/0192658 A1 | 9/2004 | Hunter et al. |
| 2004/0225077 A1 | 11/2004 | Gravett et al. |
| 2004/0228899 A1 | 11/2004 | Lee et al. |
| 2004/0230076 A1 | 11/2004 | Lifshitz-Liron et al. |
| 2005/0010305 A1 | 1/2005 | Lee |
| 2005/0026870 A1 | 2/2005 | Roldan et al. |
| 2005/0032825 A1 | 2/2005 | Metcalf, III et al. |
| 2005/0037052 A1 | 2/2005 | Udipi et al. |
| 2005/0049225 A1 | 3/2005 | Brookler |
| 2005/0054616 A1 | 3/2005 | Aronhime et al. |
| 2005/0070504 A1 | 3/2005 | Burgio, Jr. et al. |
| 2005/0246033 A1 | 11/2005 | Link |
| 2005/0272707 A1 | 12/2005 | Horowitz et al. |
| 2005/0282783 A1 | 12/2005 | Bujoli et al. |
| 2006/0166937 A1 | 7/2006 | Prescott |
| 2006/0178439 A1 | 8/2006 | Mohakhud et al. |
| 2006/0183717 A1 | 8/2006 | Du Mesnil et al. |
| 2006/0188542 A1 | 8/2006 | Bobyn et al. |
| 2006/0258625 A1 | 11/2006 | Deshpande et al. |
| 2006/0269602 A1 | 11/2006 | Dasch et al. |
| 2006/0293524 A1 | 12/2006 | Patel et al. |
| 2007/0021389 A1 | 1/2007 | Aronhime et al. |
| 2007/0021616 A1 | 1/2007 | Aronhime et al. |
| 2007/0021617 A1 | 1/2007 | Aronhime et al. |
| 2007/0021618 A1 | 1/2007 | Aronhime et al. |
| 2007/0021619 A1 | 1/2007 | Aronhime et al. |
| 2007/0027323 A1 | 2/2007 | Aronhime et al. |
| 2007/0066569 A1 | 3/2007 | Senthilkumar et al. |
| 2007/0089794 A1 | 4/2007 | Chen |
| 2007/0112197 A1 | 5/2007 | Grassi et al. |
| 2007/0173645 A1 | 7/2007 | Danda et al. |
| 2007/0191851 A1 | 8/2007 | Ashammakhi |
| 2008/0011613 A1 | 1/2008 | Wang |
| 2008/0090784 A1 | 4/2008 | Laborila et al. |
| 2008/0108588 A1 | 5/2008 | Garrett |
| 2008/0286377 A1 | 11/2008 | Healey et al. |

FOREIGN PATENT DOCUMENTS

| | | |
|---|---|---|
| JP | 2000/070288 | 10/1999 |
| WO | WO 94/14455 | 7/1994 |
| WO | WO 95/28936 | 11/1995 |
| WO | WO 99/18972 | 4/1999 |
| WO | WO 00/00177 | 1/2000 |
| WO | WO 00/64516 | 11/2000 |
| WO | WO 01/13922 | 3/2001 |
| WO | WO 01/32185 | 5/2001 |
| WO | WO 01/89494 | 11/2001 |
| WO | WO 02/083150 | 10/2002 |
| WO | WO 02/098307 | 12/2002 |
| WO | WO 03/051373 | 6/2003 |
| WO | WO 03/074098 | 9/2003 |
| WO | WO 03/093282 | 11/2003 |
| WO | WO 03/097655 | 11/2003 |
| WO | WO 03/099236 | 12/2003 |
| WO | WO 2004/024166 | 3/2004 |
| WO | WO 2004/075860 | 9/2004 |
| WO | WO 2005/000858 | 1/2005 |
| WO | WO 2005/005447 | 1/2005 |
| WO | WO 2005/044831 | 5/2005 |
| WO | WO 2005/063717 | 7/2005 |
| WO | WO 2005/063779 | 7/2005 |
| WO | WO 2005/066188 | 7/2005 |
| WO | WO 2006/134603 | 12/2006 |
| WO | WO 2007/016982 | 2/2007 |
| WO | WO 2007/032808 | 3/2007 |
| WO | WO 2007/048263 | 5/2007 |
| WO | WO 2007/048264 | 5/2007 |
| WO | WO 2007/069049 | 6/2007 |
| WO | WO 2007/083240 | 7/2007 |
| WO | WO 2007/089794 | 8/2007 |
| WO | WO 2007/109542 | 9/2007 |
| WO | WO 2007/125521 | 11/2007 |

OTHER PUBLICATIONS

Geesink, R., Hydroxyapatite-Coated Total Hip Prostheses, Clinical Orthopaedics and Related Research, 261:39-58, 1990.

Bauer, T. W. et al., Hydroxyapatite-Coated Femoral Sterns: Histological Analysis of Components Retrieved at Autopsy, J. Bone Joint Surg. 73A:1439-1452, 1991.

Pidhorz, L. E. et al., A Quantitative Study of Bone and Soft Tissues in Cementless Porous-Coated Acetabular Components Retrieved at Autopsy, J. Arthroplasty 1993, 8:213-225.

Ostovic, D. et al., Formation of a Chromophoric Complex Between Alendronate and Copper (II) Ions, Pharmaceutical Research, 10:470-472, 1993.

Denissen, Harry et al., Ceramic Hydroxyapatite Implants for the Release of bBsphosphonate, Bone and Mineral 25 (1994) 123-134.

Green, J. R. et al., Preclinical Pharmacology of CGP42'446, a New, Potent, Heterocyclic Bisphosphonate Compound, J. Bone Miner. Res. 1994, 9:745-751.

Bobyn, J. D. et al., The Susceptibility of Smooth Implant Surfaces to Peri-implant Fibrosis and Migration of Polyethylene Wear Debris, Clinical Orthopaedics. 1995, 311:21.

Ryd, L. et al., Roentgen Sereophotogrammetric Analysis as a Predictor of Mechanical Loosening of Knee prosthesis, J. of Bone and Joint Surgery, 77-B:377-383, 1995.

Horowitz, S. M. et al., Inflammatory response to implant particulates in a macrophage/osteoblast Coculture Model, Journal Article, Calcified Tissue International, (1996) 59:392-396.

Horowitz, S. M. et al., Pharmacologic Inhibition of Particulate-Induced Bone Resorption, J. Biomed. Mater. Res. 31:91-96, 1996.

Denissen, Harry et al., Degradable Bisphosphonate-Alkaline Phosphatase-Complexed Hydroxyapatite Implants in Vitro, Journal of Bone and Mineral Research, 1997, 12: 290-297.

Shanbhag, Arun S. et al., Inhibition of Wear Debris Mediated Osteolysis in a Canine Total Hip Arthroplasty Model, Clinical Orthopaedics and Related Research (1997) No. 344, p. 33-43.

Yaffe, A. et al., Local Delivery of an Amino Bisphosphonate Prevents the Resorptive Phase of Alveolar Bone Following Mucoperiosteal Flap Surgery in Rats, J. Periodontol. 1997, 68:884-889.

Pataki, A. et al., Effects of Short-Term Treatment With the bisphosphonates Zoledronate and Pamidronate on Rat Bone: A Comparative Histomorphometric Study on the cancellous Bone Formed Before, During and After Rreatment, Anat. Rec. 1997, 249:458-468.

Meraw, Stephen J. et al., Qualitative Analysis of Peripheral Peri-Implant Bone and Influence of Alendronate Sodium on Early Bone Regeneration, J. Periodontol 1999, 70:1228-1233.

Meraw, Stephen J. et al., Use of Alendronate in Peri-Implant Defect Regeneration, J. Periodontol 1999, 70:151-158.

Shanbhag, A. S. et al., Enhancing Net Bone Formation in Canine Total Hip Components With Bisphosphonates, Trans. Orthop. Res. Soc. 1999, 24:255.

Bobyn, J. D. et al., Characteristics of bone ingrowth and interface mechanics of a new porous tantalum biomaterial, J. Bone Joint Surg. 1999, 81B:907-914.

Bobyn, J. D. et al., Tissue response to porous tantalum acetabular cups: A canine model, J. Arthroplasty 1999, 14:347-354.

Overgaard, S. et al., The influence of crystallinity of the hydroxyapatite coating on the fixation of implants: mechanical and histomorphometric results, J. Bone Joint Surg. 81B:725-731, 1999.

Russell, R. G. G. et al., Bishphosphonates: from the laboratory to the clinic and back again, Bone, 25:97-106, 1999.

Binderman, I. et al., Effectiveness of local delivery of alendronate in reducing alveolar bone loss following periodontal surgery in rats, J. Periodontol 2000, 71:1236-1240.

Denissen, Harry et al., Alveolar bone response to submerged bisphosphonate-complexed hydroxyapatite implants, J. Periodontol, 2000, 71:279-286.

Denissen, Harry et al., Normal osteoconduction and repair in and around submerged highly bisphosphonate-complexed hydroxyapatite implaints in rat tibiae, J. Periodontal 2000, 71:272-278.

Shanbhag, A. S. et al., Mitogenic effects of bisphosphonates on osteoblastic cells, Trans. Orthop. Res. Soc. 2000, 25:688.

Hilding, M. et al., Clodronate prevents prosthetic migration, Acta. Orthop. Scand., 71(6):553-557, 2000.

Venesmaa, Petri K. et al., Alendronate reduces periprosthetic bone loss after uncemented primary total hip arthrophasty: A prospective randomized study, Journal of Bone and Mineral Research (2001) 16:2126-2131.

Wilkinson, J. Mark et al., Effect of pamidronate in preventing local bone loss after total hip arthoplasty: A randomized, double-blind, controlled, trial, J. Bone Miner. Res. 2001, 16:556-564.

Yoshinari, M. et al., Immobilization of biphosphonates on surface modified titanium, Biomaterials 22 (2001) 709-715.

Engh, C. A. et al., Long-term results using the anatomic medullary locking prosthesis, Clin. Orthop. 2001, 393:137-146.

D'Antonio, J. A. et al., Hydroxyapatite femoral stems for total hip arthroplasty: 10- to 13-year followup, Clin. Orthop. 2001, 393:101-111.

Little, D. G. et al., Intravenous pamidronate reduces osteoporosis and improves formation of the regenerate during distraction osteogenesis. A study in immature rabbits, J. Bone Joint Surg. (Br) 2001, 83-B:1069-1074.

Green, J. R., Chemical and biological prerequisites for novel bisphosphonate molecules: Results of comparative preclinical studies, Seminars in Oncology 28:4-10, 2001.

Bobyn et al., Marked enhancement of Bone Growth Into Porous Implants by Zoledronic Acid, 48th Annual Meeting of the Orthopaedic Research Society, Paper No. 27, 2002.

Ganguli, A. et al., The interactions of bisphosphonates in solution and as coatings on hydroxyapatite with osteoblasts, Journal of Materials Science: Materials in Medicine 13 (2002) 923-931.

Soininvaara, T. A. et al., Effect of alendronate on periprosthetic bone loss after total knee arthroplasty: A one-year, randomized, controlled trial of 19 patients, Calcif. Tissue Int. (2002) 71:472-477.

Yoshinari, M. et al., Bone response to calcium phosphate-coated and bisphosphonate-immobilized titanium implants, Biomaterials 23 (2002) 2879-2885.

Teloken, M.A. et al., Ten to fifteen-year follow-up after total hip arthroplasty with a tapered cobalt-chromium femoral component (tri-lock) inserted without cement, J. Bone Joint Surg. (Am) 2002, 84-A:2140-2144.

Sychterz, C. J. et al., What we have learned about long-term cementless fixation from autopsy retrievals, Clin. Orthop. 2002, 405:79-91.

Day, J. et al., Bisphosphonates affect the apparent modulus of trabecular bone through architecture and not mineralization, Trans. $48^{th}$ Orthop. Res. Soc. 2002, 27:85.

Kuljanin, J. et al., Spectrophotometric determination of alendronate in pharmaceutical formulations via complex formation with Fe (III) ions, Journal of Pharmaceutical and Biomedical Analysis, 28:1215-1220, 2002.

Geesink, R. G. T., Osteoconductive coatings for total joint arthroplasty, Clinical Orthopaedics and Related Research, 395:53-65, 2002.

Drentl, M. et al., Prevention of stent thrombosis following brachytherapy and implantation of drug-eluting stents, J. Interv. Cardiol. 2002, 15:477-83.

Tanzer, M. et al., Enhancement of Bone Growth into Porous Intramedullary Implants Using Non-Invasive Low Intensity Ultrasound, Journal of Orthopaedic Research, 19:195-199, 2002.

Little, D. G. et al., Zoledronic Acid Prevents Osteopenia and Increases Bone Strength in a Rabbit Model of Distraction Osteogenesis, J. Bone Miner. Res. 2003,.18:1300-1307.

Smith, E. J. et al., Zoledronic acid modulates bone repair through transiently delayed remodeling, Trans. Orthop. Res. Soc. 2003, 28:351.

Li, E. C. et al., Zoledronic acid: A new parenteral bisphosphonate, Clinical Therapeutics 25:2669-2708, 2003.

Tengvall, P. et al., Surface immobilized bisphosphonate improves stainless-steel screw fixation in rats, Biomaterials, 25:2133-2138, 2004.

Bobyn, J. D. et al., Characterization of a bisphosphonate eluting porous orthopaedic implant, $7^{th}$ World Biomaterials Congress—Sydney, Australia, 2004.

Astrand, J. et al., topical, single dose bisphosphonate treatment reduced bone resorption in a rat model for prosthetic loosening, J. of Orthopaedic Research, 22:244-249, 2004.

Bobyn, J. D. et al., Zoledronic acid causes enhancement of bone growth into porous implants, J. Bone Joint Surg. (Br) (2005) 87-B:416-20.

Josse, Solen et al., Novel biomaterials for bisphosphonate delivery, Biomaterials 26 (2005) 2073-2080.

Peter, B. et al., Calcium phosphate drug delivery system: influence of local zoledronate release on bone implant osteointegration, Bone 36 (2005) 52-60.

* cited by examiner

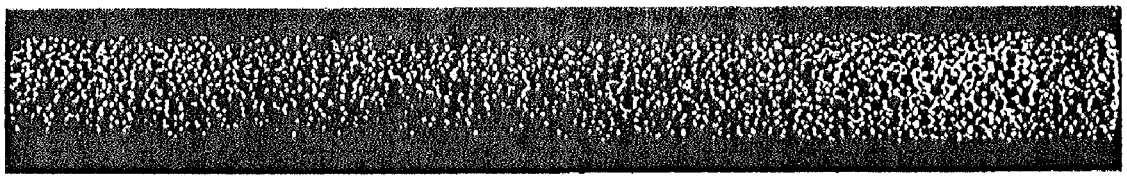
FIG_1A
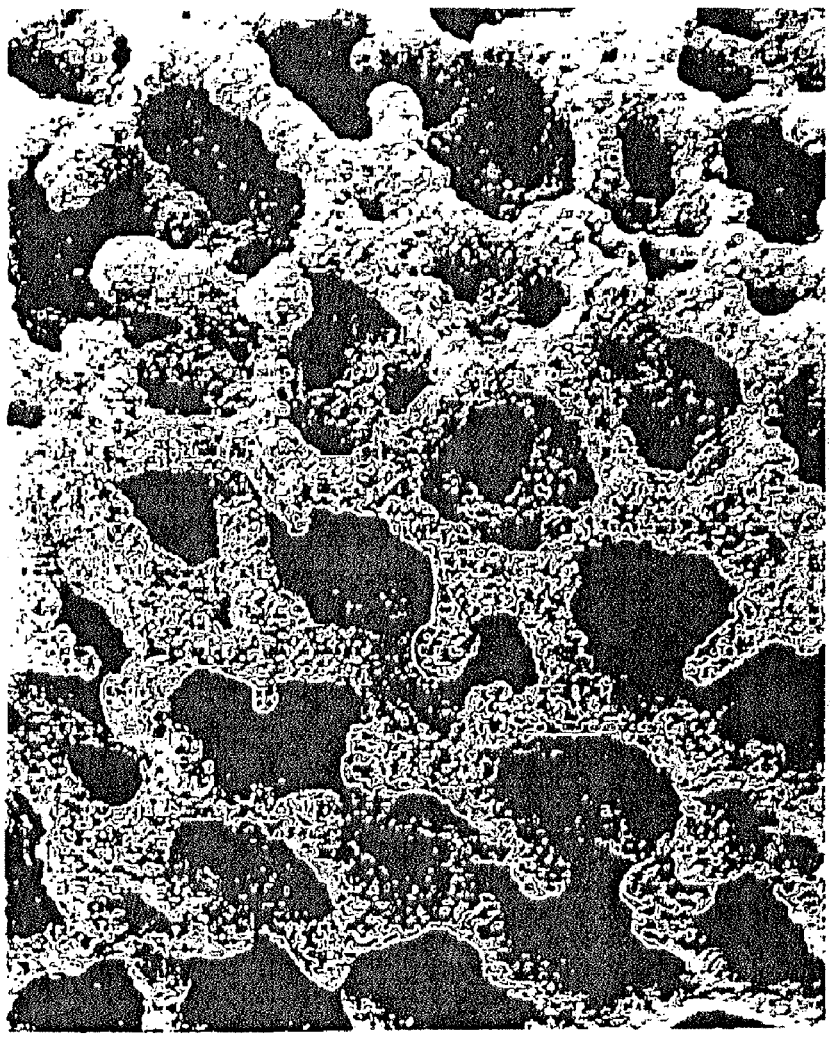
FIG_1B

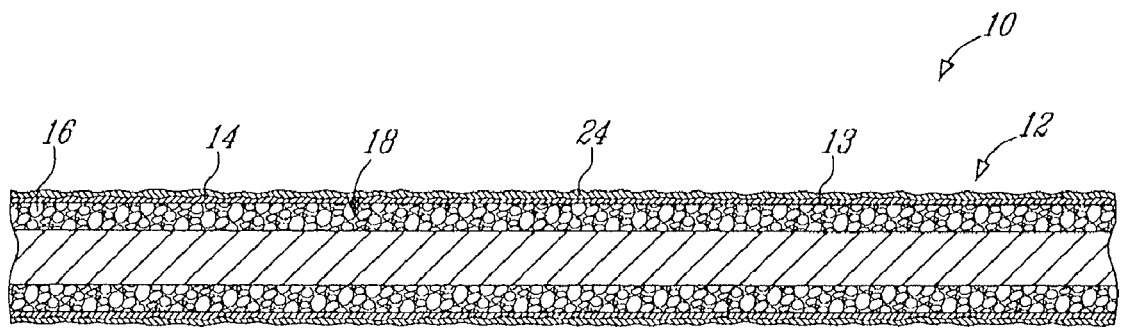
FIG_2
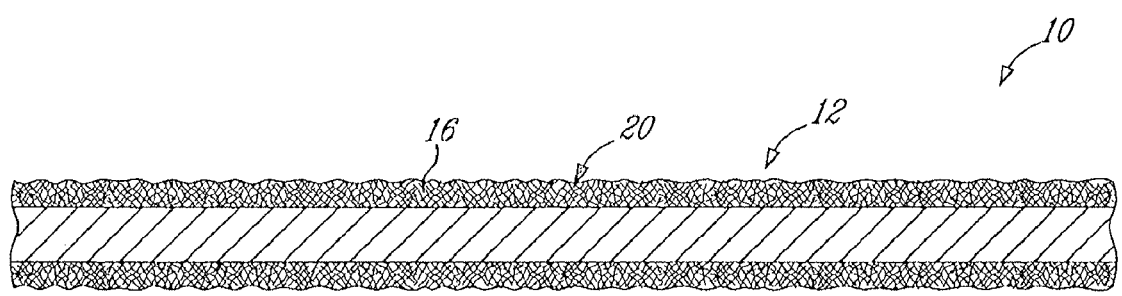
FIG_3
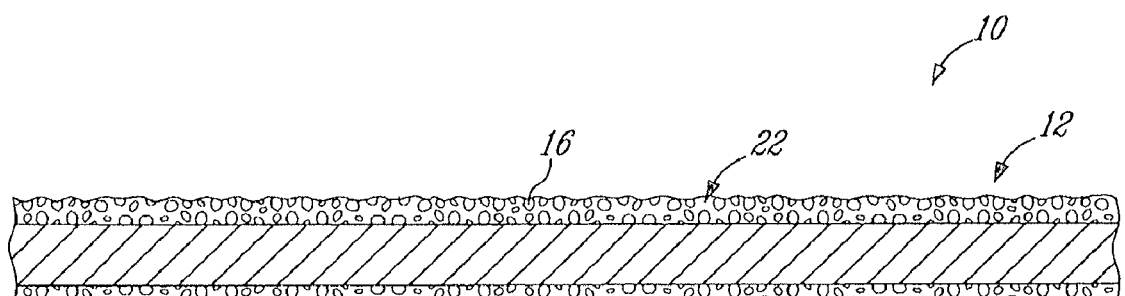
FIG_4

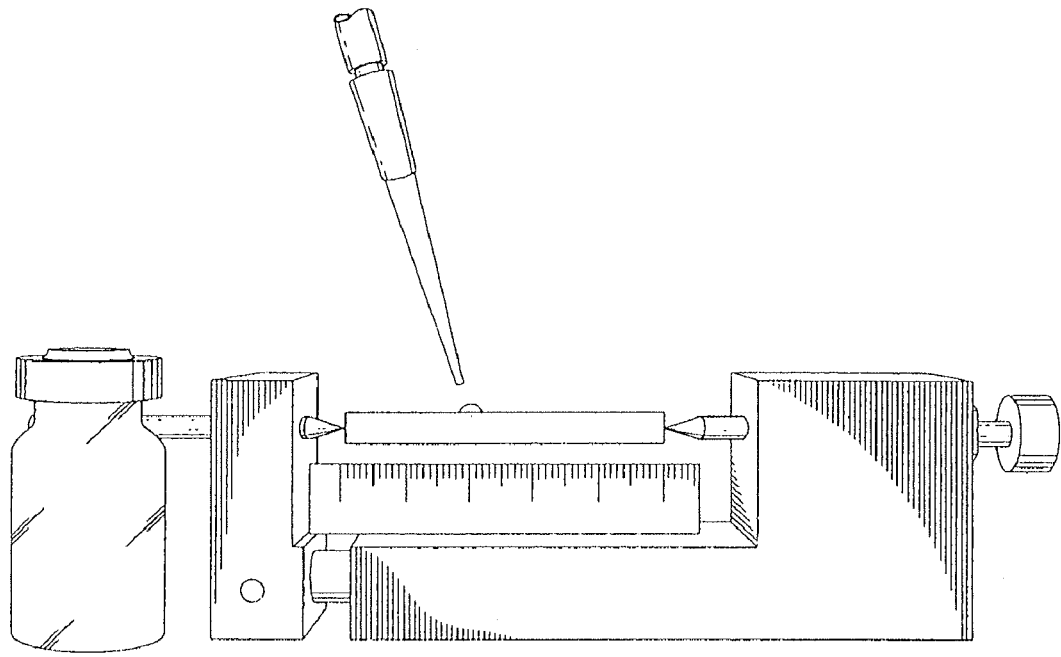
FIG_5
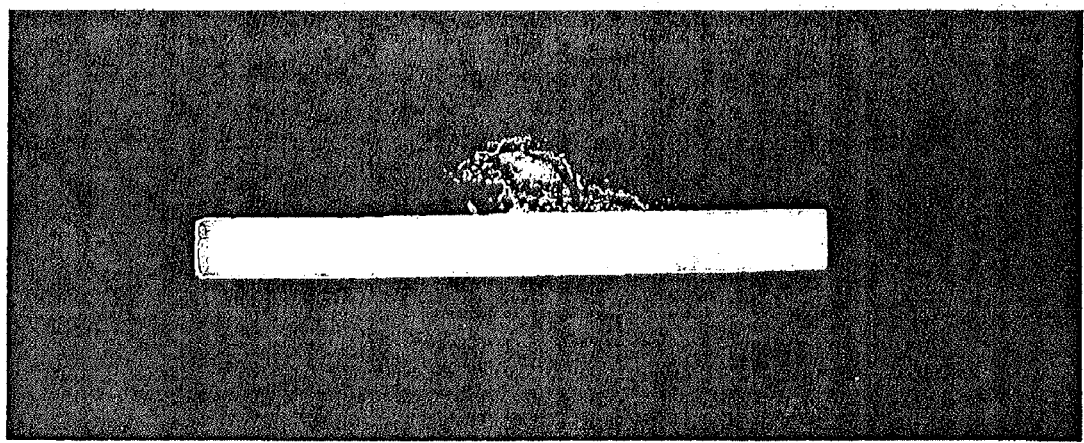
FIG_6

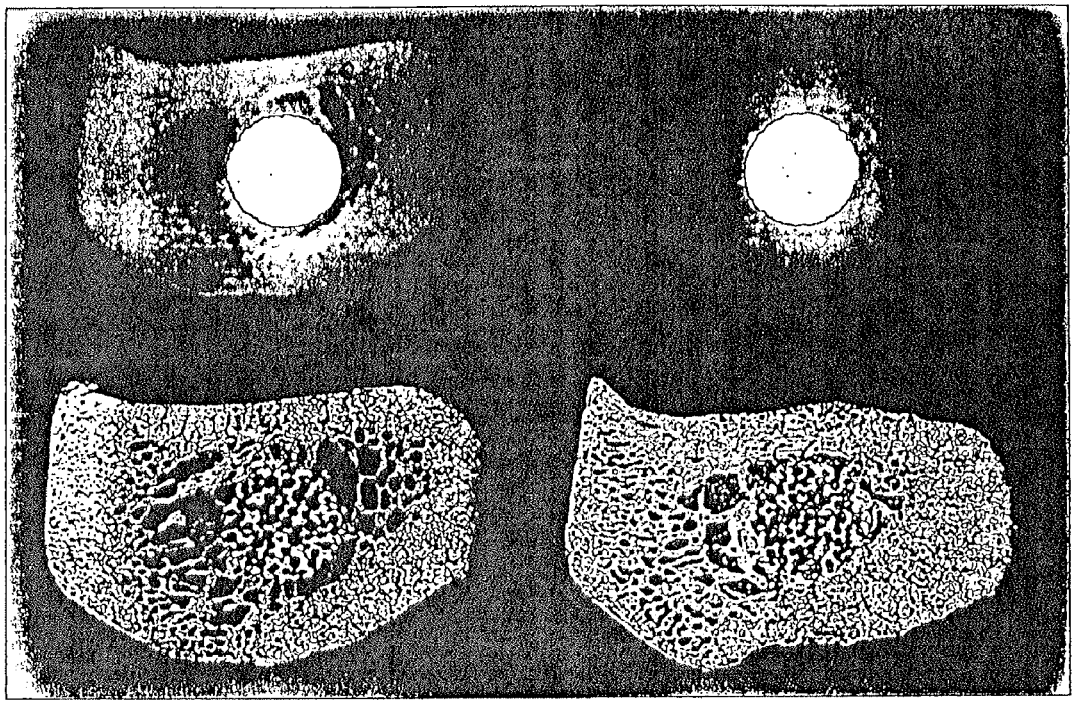
FIG_9
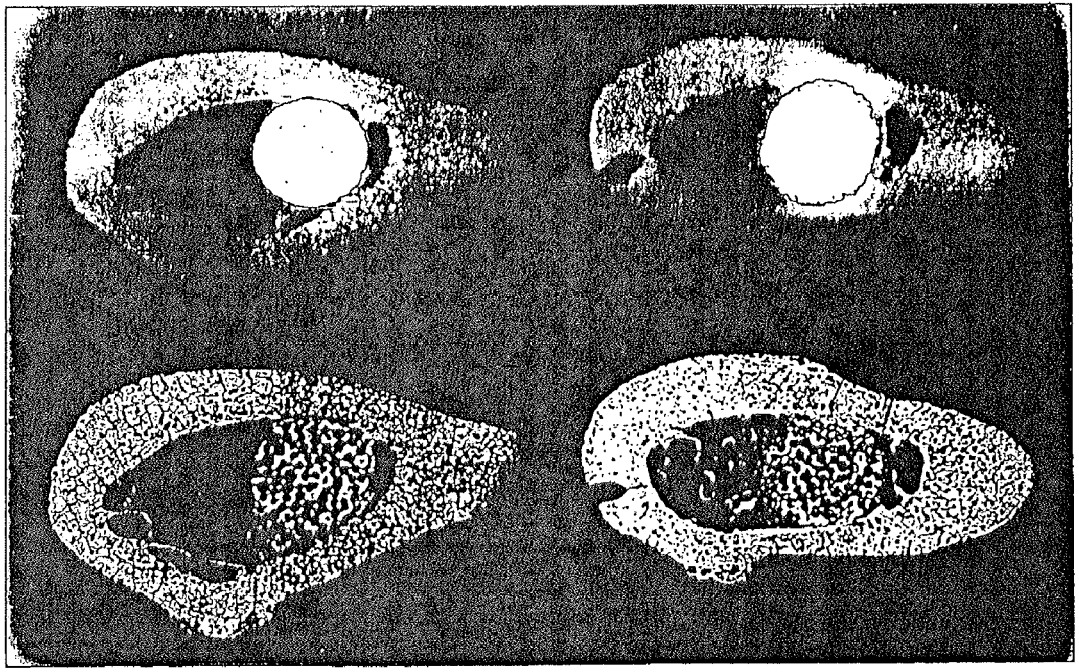
FIG_10

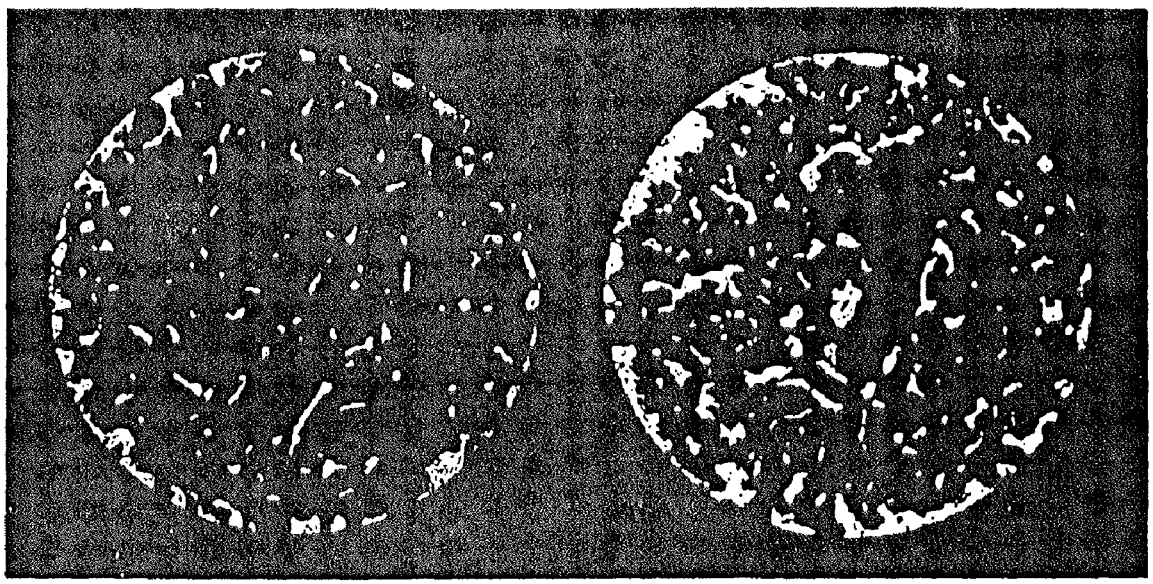
FIG_11

IMPLANT IMPROVING LOCAL BONE FORMATION

CROSS-REFERENCE TO RELATED APPLICATIONS

This application is a continuation application that claims the benefit of co-pending U.S. patent application Ser. No. 11/061,745, filed Feb. 22, 2005, which is herein incorporated by reference in its entirety.

BACKGROUND OF THE INVENTION (a) Field of the Invention
(b) Description of Prior Art Bone growth into porous materials has proven to be a very effective method for attaching prosthetic implants to the bony skeleton (Engh C A, Claus A M, Hopper R H, Engh C A. Clin Orthop 393:137-146, 2001; Teloken M A, Bissett G, Hozack W J, Sharkey P F, Rothman R H. J Bone Joint Surg [Am] 84-A:2140-2144, 2002; D'Antonio J A, Capello W N, Manley M T, Geesink R. Clin Orthop 393:101-111, 2001; Pidhorz L E, Urban R M, Jacobs JJ, Sumner D R, Galante J O. J Arthrop 8:213-225, 1993; Sychterz C J, Claus A M, Engh C A. Clin Orthop 405:79-91, 2002). However, there remains a need to develop modalities that can accelerate and/or increase biologic fixation. The more rapid and the greater the amount of bone formation around and/or within an implant, the faster the implant becomes mechanically secured against the disruptive forces of load bearing and the sooner patients can safely return to their activities of daily living. In situations where bone stock is frequently compromised, or where initial implant stability is more tenuous (such as in the elderly, post-traumatic cases, or revision surgery), both short and long-term clinical results are inferior, and the construct would clearly benefit from enhanced biologic fixation. As well, the more extensive the peri-implant tissue formation, the more protected is the bone-implant interface against wear particle induced periprosthetic osteolysis (Bobyn J D, Jacobs JJ, Tanzer M, Urban R M, Aribindi R, Sumner R, Turner T, Brooks C E, Galante J O: Clin Orthop 311:21, 1995). Increased peri-implant bone formation may also minimize the risk of postoperative periprosthetic fractures and provide additional bone stock if a subsequent revision is needed. An additional issue relates to the bone-implant interface in the immediate post-operative phase. A likely scenario for the onset of prosthetic loosening is that initial implant fixation is compromised by the resorption of the traumatized and necrotic bone adjacent to the implant. This theory is supported by the quantitative radiostereometry studies of Ryd et al (Ryd L, Albrektsson B E, Carlsson L, et al: J Bone Joint Surg [Br] 77:377-83, 1995) that showed postoperative implant migration predicts later loosening. This early migration must be related to bone resorption, since oral bisphosphonate therapy has recently been shown to reduce the initial migration of knee prostheses through its inhibitory effect on osteoclastic function (Hilding M, Ryd L, Toksvig-Larsen S, Aspenberg P: Acta Orthop Scand 71:553-7, 2000).

Various methods have been investigated to increase the rate and/or the extent of bone growth into porous implants, with varying degrees of success. Due largely to practical limitations and/or cost issues, only calcium phosphate coatings, and most notably hydroxyapatite, have to date reached the point of clinical applications. (Geesink R. Clin Orthop 225:147-170, 1990; Bauer T W, Geesink R C, Zimmerman R, McMahon J T. J Bone Joint Surg [Am] 73:1439-1452, 1991; D'Antonio J A, Capello W N, Manley M T, Geesink R. Clin Orthop 393:101-111, 2001; Overgaard S, Bromose U, Lind M, Bunger C, Soballe K. J Bone Joint Surg [Br] 81:725-731, 1999) Of particular recent interest is the use of bisphosphonates for modifying bone remodeling around orthopaedic devices. Bisphosphonates selectively absorb to bone mineral and inhibit bone resorption by interfering with the action of osteoclasts. It is believed that bisphosphonates are internalized by osteoclasts, interfere with specific biochemical processes and induce apoptosis. All bisphosphonates contain two phosphonate groups attached to a single carbon atom, forming a P—C—P structure; as such they are stable analogues of naturally occurring pyrophosphate-containing compounds. The more potent nitrogen-containing bisphosphonates, such as zoledronic acid (ZA), may affect cellular activity and cell survival by interfering with protein prenylation and therefore the signaling functions of key regulatory proteins (Russell RGG, Rogers M J: Bone 25:97-106, 1999).

Recent literature has described the utility of bisphosphonates for affecting the osteoblastic/osteoclastic cellular response in both mature and healing bone (Green JR, Müller K, Jaeggi K A. J Bone Miner Res 9:745-751, 1994; Pataki A, Muller K, Green J R, Ma Y F, Li Q N, Jee W S. Anat Rec 249:458-468, 1997). This has resulted in oral bisphosphonate therapy for helping to mitigate the osteolytic effects of accumulated wear debris around joint replacement implants (Shanbhag A S, Hasselman C T, Rubash H E. Clin Orthop 344:33-43, 1997; Shanbhag A S, May D, Cha C, Kovach C, Hasselman C T, Rubash H E. Trans Orthop Res Soc 24:255, 1999; Horowitz, S M, Algan, S A, Purdon M A. J Biomed Mater Res 31:91-96, 1996.) As well, bisphosphonates have been used to manage periprosthetic bone loss as might occur through stress shielding mechanisms (Soininvaara T A, Jurvelin J S, Miettinen H J A, Suomalainen O T, Alhava E M, Kroger P J. Calcified Tissue Int 71:472-477, 2002; Venesmaa P K, Kroger H P, Miettinen H J, Jurvelin J S, Suomalainen O T, Alhava E M. J Bone Miner Res 16:2126-2131, 2001; Wilkinson J M, Stockley I, Peel N F, Hamer A J, Elson R A, Barrington N A, Eastell R. J Bone Miner Res 16:556-564, 2001). Also of important note is that Hilding et al (Hilding M, Ryd L, Toksvig-Larsen S, Aspenberg P: Acta Orthop Scand 71:553-7, 2000) showed an early postoperative oral regimen of clodronate reduced migration of knee prostheses, as measured by radiostereometry. In experimental rabbit studies, Little et al (Little DG, Cornell M S, Briody J, Cowell C T, Arbuckle S, Cooke-Yarborough C M. J Bone Joint Surg [Br] 83-B:1069-1074, 2001) have shown that in distraction osteogenesis a single postoperative intravenous dose of pamidronate (3 mg/kg) decreased the disuse osteopenia normally associated with lengthening and increased the amount and density of the regenerate bone. In a further study, Little et al (Little DG, Smith N C, Williams P, Briody J, Bilston, L, Smith EJ, Gardiner E M, Cowell C T. J Bone Miner Res 18:1300-1307, 2003) showed that one or two doses of the more potent ZA abolished osteopenia and increased regenerate volume, mineralization and strength.

There has been speculation about the possibility of bisphosphonates acting not only to suppress osteoclastic activity but also to stimulate osteoblastic activity (Green J R, Muller K, Jaeggi K A. J Bone Miner Res 9:745-751, 1994; Pataki A, Müller K, Green J R, Ma Y F, Li Q N, Jee W S. Anat Rec 249:458-468, 1997; Shanbhag A S, Kenney J, Manning C, Flannery M, Rubash H, Harris W, Goldring S. Trans Orthop Res Soc 25:688, 2000). However, recent findings by Smith et al (Smith EJ, Bugler R J, Peat R A, McEvoy A, Briody J N, Baldock P A, Eisman J A, Little DG, Gardiner E M. Trans Orthop Res Soc 28:351, 2003) have shown that the increase in net bone accumulation from ZA were due to an increase in retention of callus; the bone formation rate was actually reduced. Modulation of bone turnover shifted the balance of formation and resorption in a favorable manner resulting in a net increase in total regenerate at six weeks. Remodeling took place over 45 weeks in this model, indicating that the effects of ZA are long lasting.

On a cost basis alone, bisphosphonates could have a substantial advantage over recombinant proteins for improving the bone healing response within and around orthopaedic implants. Although intravenous delivery of ZA is both feasible and convenient, it subjects the patient to various systemic and potentially adverse effects.

Local delivery of medicinal products for implants of various types has been attempted, however with varying degrees of success. For example, anti-inflammatory agents delivered to coronary stent implant sites have been shown to increase patency rates. Local delivery of bisphosphonates in dental surgical applications has also recently been attempted. For example, local application of alendronate, a second generation bisphosphonate, following periodontal surgery in rats has been shown to reduce alveolar bone resorption. (Binderman I, Adut M, Yaffe A: J Periodontol 71:1236-40, 2000; Yaffe A, lztkovich M, Earon Y, Alt I, Lilov R, Binderman: J Periodontol 68:884-9, 1997) Another rat study has further shown that a single application of alendronate via a sponge to an implant site reduces the amount of soft tissue that forms as a consequence of resorptive remodeling from repetitive implant motion (Astrand J, Aspenberg P: J Orthop Res 22:244-249, 2004).

The concept of immobilizing a bisphosphonate compound via hydroxyapatite has previously been explored for dental surgical applications, particularly in the context of smooth surface tooth root implants. (Meraw S J and Reeve C M., Qualitative analysis of peripheral pen-implant bone and influence of alendronate sodium on early bone regeneration, J Peridontology 70:1228-1233, 1999; Yoshinari M, et al., Bone response to calcium phosphate-coated and bisphosphonate-immobilized titanium implants, Biomaterials 23:2879-2885, 2002; Ganguli A, et al, The interaction of bisphosphonates in solution and as coatings on hydroxyapatite with osteoblasts, J Mater Sci: Mater Med 13:923-931, 2002; Denissen H, et al, Normal osteoconduction and repair in and around submerged highly bisphosphonate-complexed hydroxyapatite implants in rat tibiae, J Periodontology 71:272-278, 2000). These studies have shown that local release of bisphosphonate compounds, bound to dental implants through an intermediary hydroxyapatite coating, results in a net gain in peri-implant bone formation. However, the extent of bone formation around the bisphosphonate coated implants shown by these studies remains relatively low compared to the control specimens. Therefore, however positive, relatively limited benefits with respect to bone formation have resulted.

Therefore, while the local delivery of bisphosphonate to an implant site for improving the bone healing response within and around the implant is desirable, the means by which the medicinal compounds are locally administered poses challenges for many implant applications. As such, a need exists for an improved means and method for administering a local release of bisphosphonate to allow the compound to positively affect peri-implant bone remodeling, while avoiding the systemic exposure. . Further, a need exists to improve the extent of bone formation by such locally released bisphosphonate.

It would therefore be highly desirable to be provided with a new implant improving bone formation around and/or within the implant.

SUMMARY OF THE INVENTION

In accordance with one aspect of the present invention there is provided a porous implant comprising a porous portion coated with a calcium phosphate compound, said implant having been contacted with a bisphosphonate compound to form a bisphosphonate layer chemically bound to said calcium phosphate compound at the surface of said portion and bisphosphonate molecules being non-chemically attached inside pores of said portion, said non-chemically attached bisphosphonate molecules being burst-releasable in a subject upon contact with body fluids and said chemically bound bisphosphonate layer being slowly releasable in said subject upon contact with said body fluids.

In accordance with another aspect of the present invention, there is also provided a porous bone implant comprising a porous portion coated with a calcium phosphate compound on an outer surface thereof and having a bisphosphonate compound applied to said porous portion to form a bisphosphonate layer chemically bound to said calcium phosphate on said outer surface of said porous portion, said bisphosphonate layer being releasable from the implant to promote bone formation around and/or within said implant when implanted in said subject.

There is also provided, in accordance with another aspect of the present invention, a biocompatible bone implant comprising a bone growth stimulating portion having at least a first region with a calcium phosphate coating thereon and at least a second region free of said calcium phosphate, said bone growth stimulating portion having a bisphosphonate compound applied thereto to form a bisphosphonate layer chemically bound to said calcium phosphate over said first region and bisphosphonate molecules being non-chemically attached to said bone growth stimulating portion over said second region, wherein said bisphosphonate compound is released from said first and second regions at different rates when said implant is installed within a subject.

There is further provided, in accordance with another aspect of the present invention, a biocompatible bone implant comprising a bone growth stimulating active agent on at least a portion thereof, said active agent being locally deliverable to bone proximate said implant in at least a two-phased release scheme, wherein a first phase rapidly releases a first quantity of said active agent and at least a second phase gradually releases a second quantity of said active agent, whereby bone formation stimulated by said active agent is modulated.

In one embodiment of the present invention, the implant is for replacement of a joint such as, but not limited to hip, knee, elbow, ankle and shoulder. In an alternate embodiment, the implant includes a spine or dental implant.

In one embodiment of the present invention, the implant is entirely porous.

In a preferred embodiment of the present invention, the implant includes at least a porous portion which comprises a biocompatible surface having interconnecting pores formed therein. Alternatively, the biocompatible surface may be a sintered bead porous surface, a fiber metal porous surface, a textured surface, a plasma spray surface, or any other type of surface that one skilled in the art would envision as being suitable for the purpose of the present invention.

In one embodiment of the present invention, the implant is made from a material comprising at least one of titanium, titanium-based alloy, zirconium, niobium, cobalt-based alloy, tantalum and polymer composite. In a preferred embodiment of the present invention, wherein the implant includes a porous portion, the pores in the implant are of a size ranging from about 20 to about 1000 μm, more preferably the pores are of an average size of about 100 to about 700 μm.

In a preferred embodiment of the present invention, the bisphosphonate is at least a third generation bisphosphonate, such as one of bisphosphonate zoledronic acid (ZA), ibandronate and risedronate, for example. Most preferably, the selected third generation bisphosphonate is bisphosphonate zoledronic acid (ZA). While it is to be understood that the present invention may employ any bisphosphonate compound, at least third generation bisphosphonate compounds (i.e. third generation or later) are preferably used due to their improved potency over earlier generations. However, examples of first and second generation bisphosphonates which can nonetheless be used, however may be less effective, include: etidronate; clodronate; tiludronate; pamidronate; dimethyl pamidronate; and alendronate. It is also contemplated that subsequent generations of bisphosphonate compounds, having further improved potency, may also be employed as they become available.

The term "bisphosphonate of the third generation" or "third generation bisphosphonate" is widely used and accepted in the literature, and therefore one skilled in the art will understand which bisphosphonate compounds constitute third generation compounds. For example, such third generation bisphosphonates include zolendronate (zoledronic acid), risendronate and ibandronate.

All references herein are hereby incorporated by reference.

BRIEF DESCRIPTION OF THE DRAWINGS

FIG. 1A is a photograph of an HA-coated porous tantalum ulnar implant dosed with 0.05 mg zoledronic acid.

FIG. 1B is a scanning electron micrograph of the HA-coated pores.

FIG. 2 is a cross-sectional view of an embodiment of the present invention where the porous portion may be a porous material of a sintered bead surface for example, wherein the binding agent and the active agent applied thereto are schematically depicted.

FIG. 3 is a cross-sectional view of an alternative embodiment of the present invention where the porous portion is made of fiber metal.

FIG. 4 is a cross-sectional view of an alternative embodiment of the present invention where the porous portion is made of a textured surface.

FIG. 5. illustrates spindle fixture used for manual dosing of implants with zoledronic acid in aqueous solution with dosing pipette and vial of Zometa™.

FIG. 6. is a post-mortem contact radiograph illustrating position of an intramedullary implant within the ulna.

FIG. 9. is a representative contact radiographs (top) with corresponding backscattered scanning electron micrographs (bottom) of control (left) and ZA-dosed (right) implant sections taken in the metaphysis. Note the additional bone filling the intramedullary canal in the ZA-dosed section.

FIG. 10. is a representative contact radiographs (top) with corresponding backscattered scanning electron micrographs (bottom) of control (left) and ZA-dosed (right) implant sections taken in the diaphysis. Additional bone is clearly visible in the ZA-dosed section.

FIG. 11. is a backscattered scanning electron micrographs of a control section (left, 12.5% ingrowth) and a ZA-dosed section (right, 19.8% ingrowth) selected for the extent of bone ingrowth precisely corresponding to the mean for each group. The implant and surrounding bone were digitally subtracted from the images to clarify the illustration. The implant diameter is 5 mm. Note the tendency for more bone at the periphery where the implants are HA-coated but the presence of bone islands throughout the cross-sections.

DETAILED DESCRIPTION OF THE INVENTION

The hypothesis that bisphosphonates have a positive effect on net bone growth, particularly into porous implants, was first confirmed by conducting a canine ulnar intramedullary implant model in which porous tantalum rods were implanted for 6 weeks. (Bobyn J D, Tanzer M, Harvey EJ, Krygier JJ, Little DG. J Bone Joint Surg (Br), 2005) Immediately after surgery, seven test animals with 14 ulnar implants were administered a single intravenous dose of 0.1 mg/kg ZA (Novartis Pharma A G, Basel, Switzerland). Because of the systemic exposure of test animals to ZA it was necessary to utilize external control data from a prior experiment (Tanzer M, Kantor S, Bobyn J D. J Arthrop 19:195-199, 2002) for comparisons of bone ingrowth. The mean extent of bone ingrowth was 6.6% for the control implants and 12.2% for the ZA-treated implants, a relative difference of 85% that was statistically significant. Detailed quantitative analysis of the individual islands of new bone formation with the implant pores revealed that the number of bone islands was similar for both implant groups but the average bone island size was 69% larger in the ZA-treated group. This finding was consistent with the documented suppression of osteoclastic remodeling with bisphosphonate therapy (Day J, Ding M, Bednarz P, Van Der Linden J, Mashiba T, Hirano T, Johnston C, Burr D, Hvid I, Sumner D, Weinans H. Trans 48th Orthop Res Soc 27:85, 2002) and the study of Smith et al (Smith EJ, Bugler R J, Peat R A, McEvoy A, Briody J N, Baldock P A, Eisman J A, Little DG, Gardiner E M. Trans Orthop Res Soc 28:351, 2003) suggesting that osteoblastic activity is not increased in the presence of bisphosphonates.

Thus, delivery of a bone stimulating active agent such as bisphosphonate to an implant site for improving the bone healing response within and around the implant is effective. The preferred embodiments of the present invention as described below further provide an improved local delivery means of the bisphosphonate active agent, enabling a modulated delivery of the active agent from the implant which promotes bone formation around and/or into the implant. More particularly, the present invention preferably provides at least a biphasic release of the bisphosphonate compound.

Figure 1C:
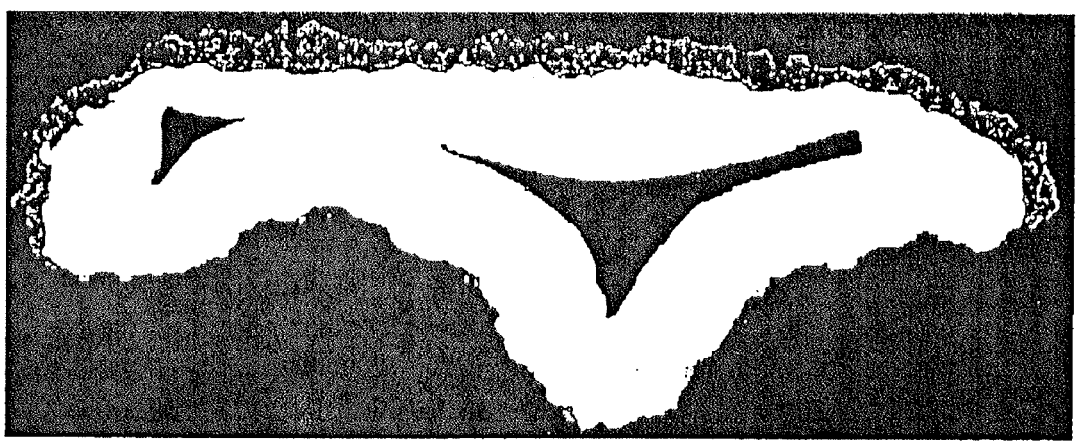
FIG. 1C is a backscattered scanning electron micrograph illustrating the HA coating on the superficial tantalum struts. The tantalum struts appear as white in the backscattered images, HA as light grey.
Figure 1D:
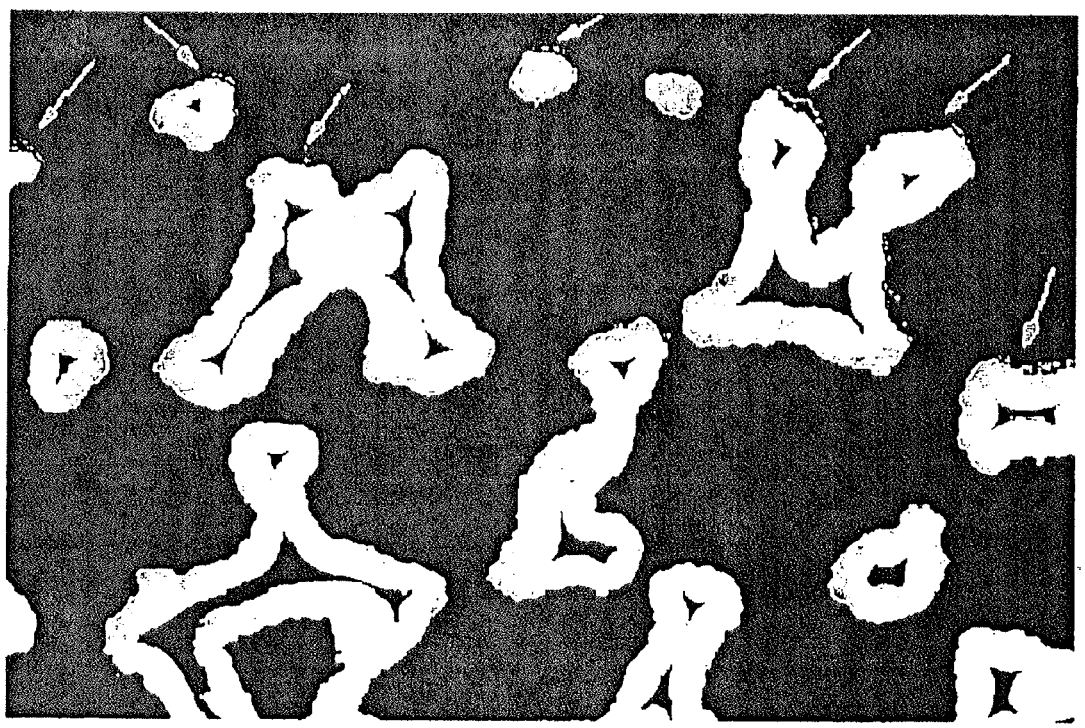
FIG. 1D is a backscattered scanning electron micrograph illustrating the HA coating (see arrows) on the superficial tantalum struts. The tantalum struts appear as white in the backscattered images, HA as light grey.

Referring to FIGS. 1a-4, an implant 10 comprises at least a bone growth stimulating portion 12 around and/or within which bone proximate thereto is capable of growing such that the surrounding bone fuses with the implant. The implant 10 preferably includes the bone growth stimulating portion 12 on at least a portion of an outer surface thereof which is adapted to be proximate to a bone surface when the implant 10 is installed within the receiving subject, whether patient, test animal or cadaver. Preferably, the bone growth stimulating portion 12 covers the complete outer surface of the implant 10, however the implant 10 may include discrete bone growth stimulating portions 12 only on selected portions thereof. Alternately, and in one preferred embodiment as depicted in FIG. 1, the implant 10 may be completely composed of such a bone growth stimulating portion 12. Preferably, the bone growth stimulating portion 12 is porous, having a plurality of interconnecting pores 16 formed therein. As such the bone growth stimulating portion 12 will be referred to herein as a porous portion 12 in accordance with a embodiment, however it is to be understood that other suitable material structures maybe used which are biocompatible and upon and around which bone may grow.

A layer of binding agent 14 is applied to at least the outer surface 13 of the porous bone growth stimulating portion 12 of the implant 10, thereby coating this outer surface 13 thereof. The binding agent 14 is one which has an affinity to bone for engagement therewith, and with which the active agent will chemically bind. Preferably, the binding agent 14 comprises a calcium phosphate compound and the active agent comprises a bisphosphonate which will chemically bind to the calcium phosphate substrate layer. The term chemically bound as used herein is intended to include covalent and ionic bonds which may form to removably engage the active agent to the binding agent. In the embodiment described in greater detail below, the calcium phosphate binding agent 14 comprises hydroxyapatite (HA), however other calcium phosphate formulations may also be used, such as tricalcium phosphate for example, or any mixture of tricalcium phosphate and HA. Although HA is used in the examples below, both HA and tricalcium phosphate are known calcium phosphates employed in various biomedical applications, particularly as biocompatible coatings on dental and hip implants.

Due to the porous nature of the bone growth stimulating portion 12, the calcium phosphate binding agent 14 applied thereto preferably covers the outer surface 13 of the implant, while the internal surfaces of pores 16 within the portion 12 remain substantially uncoated. However, depending on the method employed to apply the calcium phosphate compound to the implant, a quantity calcium phosphate may enter the inner pores 16 within the implant. The majority of the calcium phosphate compound applied, however, will tend to form a layer on the outer surface of the implant. Various methods may be used to apply the calcium phosphate compound to the implant may be used, such as chemical deposition and plasma spray deposition for example, which are well known in the art. In the embodiment described below, plasma spray deposition is used to apply the calcium phosphate to the implant. As this application technique requires physically spraying a liquid based form of the calcium phosphate directly onto the implant, mainly the outer surface thereof is coated, leaving the inner pores relatively free of the calcium phosphate compound.

The porous portion 12 of the implant 10 having the calcium phosphate binding agent applied thereto is then contacted with an active agent to form a layer 24 of said active agent which chemically binds to the binding agent 14 on the outer surface 13 of the porous portion 12. The active agent acts to stimulate bone formation when released to the surrounding bone within which the implant is disposed. In the preferred embodiment of the present invention, the active agent employed is a bisphosphonate compound which chemically binds to the calcium phosphate. The active agent is applied to the implant such that it coats at least a majority of the bone growth stimulating portion 12 thereof, both those with and without the binding agent thereon. Thus, the active agent attaches to the implant over regions which are substantially free of the binding agent, as well as those which have the binding agent thereon. In the preferred embodiment, the bisphosphonate molecules which are provided within the pores 16 become physically attached (i.e. non-chemically bound) to the porous surfaces below the outer surface of the implant due to the relative absence of the calcium phosphate thereon. The release rate of the bisphosphonate chemically bound to the calcium phosphate from the implant 10 to a surrounding bone structure differs from that of the non-chemically bonded bisphosphonate. This accordingly provides a biphasic elution profile of the bisphosphonate compound from the implant 10, as will be described further below.

In a preferred embodiment, a porous implant 10 promoting bone formation around and/or within the implant when implanted in a subject, the implant 10 comprising a porous portion 12 coated with a calcium phosphate 14, such as hydroxyapatite, having been contacted with a bisphosphonate compound, preferably a third generation bisphosphonate such as zoledronic acid, to form a bisphosphonate layer chemically bound to the hydroxyapatite on at least a partial region of said porous portion 12.

Preferably the physical structure of the implant, or at least the bone growth stimulating portion thereof, allows a first region (for example the outer surface) to be coated with a binding agent such as calcium phosphate while at least a second region thereof (for example the inner surfaces of the pores formed therein) remains substantially free of the binding agent. Thus, once by the first and second regions are coated by an active agent, such as a bisphosphonate, the active agent will release from each of the first and second regions of the implant at different release rates. However, it nevertheless remains possible to achieve such a biphasic release rate, or even a multi-phasic release rate of the active agent, by alternately providing different binding agents to the first and second regions. For example, a first calcium phosphate formulation is applied to a first region of the bone implant and a second, different, calcium phosphate formulation is applied to a second region of the bone implant. Both the first and second regions are coated with a bisphosphonate active agent, which chemically bonds to each of the calcium phosphate binding agents. However, the release rate of the bisphosphonate active agent from each of the two calcium phosphate binding agents will be different, thus providing a biphasic release of the active bisphosphonate to the surrounding bone. The present invention therefore includes such alternate means of achieving local, multi-phasic release of the bone formation stimulating active agent from the implant to the surrounding bone in order to promote and modulate bone formation.

Although the bone growth stimulating portion 12 is preferably porous, other suitable bone growth stimulating structures may also be used, providing such structures are biocompatible and permit bone formation around and/or within this region of the implant. Particularly, such structures enable portions thereof to be coated with a binding agent, such as a calcium phosphate and more preferably such as hydroxyapatite, while others remain uncoated. For example, a surface having grooves rather than pores, or alternately having other forms of surface features such as depressions and/or raised portions, may also be used. Further, while such structural surface and/or material features enable a practical means of coating only certain regions of the implant with hydroxyapatite while others remain uncoated, it is to be understood that a similar effect may be achieved on a relatively level outer surface of the implant by selectively applying the hydroxyapatite to predetermined surface regions thereof, while other surrounding regions remain bare. This may be done, for example, by masking regions of the implant not to be covered by binding agent prior to the application thereof.

The biocompatible surface of the bone growth stimulating portion may also be a sintered bead porous surface 18 as shown in FIG. 2, a fiber metal porous surface 20 as shown in FIG. 3, a textured surface 22 as shown in FIG. 4, a plasma spray surface or any other type of surface that one skilled in the art would envision as being suitable for the purpose of the present invention.

A preferred embodiment of the present invention is described below.

Materials and Methods

Binding of Bisphosphonate. A simple and effective method for binding a bisphosphonate to an orthopaedic implant involves coating it with a thin layer of a calcium phosphate such as hydroxyapatite and depositing the bisphosphonate in aqueous solution directly onto the implant. This technique takes advantage of the known chemical affinity of bisphosphonates for calcium phosphate, the same affinity that enables their selective binding to bone.

Rationale for Zoledronic Acid. Zoledronic acid (ZA), or zolendronate, is a 3rd generation bisphosphonate compound which was utilized for all studies. ZA is structurally similar to other bisphosphonates, having the required phosphorus-carbon-phosphorus structure, as shown below.

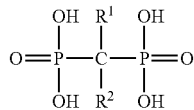

Third generation bisphosphonates generally include a hydroxyl group, associated with enhanced binding to bone, which is present in the $R^1$ position. An additional imadazole group containing two nitrogens at the $R^2$ position distinguishes ZA from other bisphosphonates. This substituent at the $R^2$ makes ZA acid 100 and 250 times more potent than 2nd generation compounds such as pamidronate and alendronate, respectively (Green, J R. Results of comparative preclinical studies. Seminars in Oncology 28:4-10, 2001; Li E C and Davis L E. Clinical Therapeutics 25:2669-2708, 2003). Table 1 below list examples of bisphosphonates, identified by generation, with their $R^1$ and $R^2$ components.

TABLE 1

| Bisphosphonate | Generation | $R^1$ | $R^2$ |
| --- | --- | --- | --- |
| Etidronate | $1^{st}$ | OH | $CH_3$ |
| Clodronate | $1^{st}$ | Cl | Cl |
| Tiludronate | $1^{st}$ | H | $CH_2SPhenyl-Cl$ |
| Pamidronate | $2^{nd}$ | OH | $CH_2CH_2NH_2$ |
| Dimethyl pamidronate | $2^{nd}$ | OH | $CH_2CH_2N(CH_3)_2$ |
| Alendronate | $2^{nd}$ | OH | $CH_2CH_2CH_2NH_2$ |
| Ibandronate | $3^{rd}$ | OH | $CH_2CH_2N(CH_3)(Pentyl)$ |
| Risendronate | $3^{rd}$ | OH | $CH_2$-3-pyridine |
| Zolendronate | $3^{rd}$ | OH | $CH_2(1H$-imidazole-1-yl$)$ |

The potency of bisphosphonates in inhibiting bone resorption appears to be dependent largely on the R2 side chain. In particular, those bisphosphonates containing a nitrogen atom at a critical distance from the P—C—P group and in specific spatial configuration are considerably more potent than non-nitrogen containing bisphosphonates. For example, second generation bisphosphonates such as pamidronate and alendronate that contain a basic primary nitrogen atom in an alkyl chain, are approximately 10-100 fold more potent than first generation bisphosphonates such as etidronate or clodronate. Third generation bisphosphonates which contain a tertiary nitrogen, such as ibandronate, risendronate and zoledronate, are even more potent at inhibiting bone resorption. Replacement of one phosphate group with a carboxylate group or methylation of phosphonate by replacement of a hydroxyl group results in similar affinity for bone, although very different anti-resorptive potencies. Thus, the two phosphonate groups are required both for targeting to bone and for the molecular mechanism of action. Although the bisphosphonate most preferably used in the present invention is ZA, another third generation bisphosphonate can also be used. While less effective, bisphosphonate compounds of earlier generations may also be employed, however it is understood that results may be less marked. Further, it is to be understood that subsequent, more potent, generations of bisphosphonates may also be employed in accordance with the present invention as these become available.

Rationale for Implant Material. A porous tantalum biomaterial was utilized for the in vivo studies (FIG. 1). The rationale for this selection was multi-factorial. The 80% volume porosity of porous tantalum provides a very open structure into which bone can heal, virtually unimpeded by the material, without the need for a solid substrate. The stiffness of porous tantalum is very low, ~3 GPa, within the stiffness of range of bone and 5-10 times less stiff than other porous coatings such as titanium fiber metal sintered beads. For in vivo studies this is important because it minimizes any stress shielding effects the implant might have on bone healing and remodeling, thus maximizing the ability to detect the effect of bisphosphonate release on bone ingrowth/remodelling. The porous tantalum material has been characterized for its bone ingrowth characteristics in prior implant models (Bobyn J D, Tanzer M, Harvey EJ, Krygier JJ, Little DG. J Bone Joint Surg (Br), In press, 2005; Bobyn J D et al: J Bone Joint Surg [Br]81:907-914, 1999; Bobyn J D, Toh K-K, Hacking S A, Tanzer M, Krygier JJ: J Arthrop 14:347-354, 1999).

As noted above, although tantalum was used in one embodiment, the implant may be made from a material comprising at least one of titanium, titanium-based alloy, zirconium, niobium, cobalt-based alloy, tantalum, and a polymer composite.

Implants 5 mm in diameter and 50 mm in length (FIG. 1) were manufactured for use in a canine ulnar intramedullary model.

Rationale for Hydroxyapatite Coating. Hydroxyapatite (HA) coatings deposited by plasma spray techniques have been successfully utilized in joint replacement implants for almost two decades (Geesink R. Clin Orthop 261:39-58, 1990; Bauer T W, Geesink R C, Zimmerman R, McMahon J T. J Bone Joint Surg [Am] 73:1439-1452, 1991; D'Antonio J A, Capello W N, Manley M T, Geesink R. Clin Orthop 393: 101-111, 2001; Overgaard S, Bromose U, Lind M, Bunger C, Soballe K. J Bone Joint Surg [Br] 81:725-731, 1999). Although the typical thickness of HA coatings used clinically is ~50 micrometers, a thinner coating of 10-15 micrometers was utilized so there was less occlusion or alteration of the pore size and pore interconnectivity. Because the plasma spray technique is line-of-sight, only the superficial struts comprising the porous tantalum structure were coated (FIG. 1). The HA coating was commercially applied in the same manner as clinically used coatings (but thinner). The methodology of applying HA coating was highly reproducible since it was computer controlled and involved identical coating amount for each implant. The final chemistry of the HA coating was well controlled thereby ensuring uniformity of ZA deposition and binding from implant to implant. HA specifications were 98% HA, 99% dense, 64% crystalline and a calcium:phosphate ratio of 1.67. Other calcium phosphates may also be used, and will have parameters with respect to density, crystalinity, etc which differ from those of HA.

As noted above, HA is but one calcium phosphate compound which may be used. Examples of other calcium phosphates which are of biomaterials interest and may be used are listed in Table 1.1 below. It is understood that any mixtures of these calcium phosphates may also be used. Amorphous calcium phosphate is a phase which is often formed during high temperature processing, such as when plasma spraying hydroxyapatite. Hydroxyapatite is the least soluble of the calcium phosphates listed, and is the most stable at pH's above 4.2. Therefore, under normal physiological conditions of pH 7.2, hydroxyapatite is preferred. The term hydroxyapatite as used herein is intended to refer to the calcium phosphate compound pentacalcium hydroxyl apatite identified on the table below.

TABLE 1.1

| Chemical Name | Abbr | Chemical Formula | Phase | Ca:P |
|---|---|---|---|---|
| Amorphous calcium phosphate | ACP | — | — | — |
| Dicalcium Phosphate | DCP | $CaHPO_4$ | Monetite | 1.00 |
| Tricalcium Phosphate | α-TCP | $Ca_3(PO_4)_2$ | | 1.50 |
| Tricalcium Phosphate | β-TCP | $Ca_3(PO_4)_2$ | Whitlockite | 1.50 |
| Pentacalcium Hydroxyl Apatite | HAp | $Ca_{10}(PO_4)_6(OH)_2$ | Hydroxyapatite | 1.67 |
| Tetracalcium Phosphate Monoxide | TTCP | $Ca_4O(PO_4)_2$ | Hilgenstockite | 2.00 |

Method for Applying/Binding ZA to Porous Tantalum Implants. ZA was obtained through our hospital pharmacy under the trade name Zometa™ (Novartis, Basel, Switzerland). Zometa™ is packaged in vials of powder that contain 4.0 mg ZA, 220 mg mannitol (a sugar bulking agent), and 24 mg sodium citrate (a buffer). The powder was mixed with distilled water and an aliquot representing a specified amount of ZA was collected in a micropipette. The micropipette was used to deposit the solution over the length of each of the small (5×50 mm) porous tantalum implants. This was done in a systematic manner, with the implants held at its ends in a spindle, and equal sized drops of solution manually deposited at 0.5 cm intervals along the implant length and 90 degree intervals around its circumference (FIG. 5). The concentration of the ZA in solution was adjusted so that about 0.5 ml of solution was required/utilized for deposition over the entire surface of the porous tantalum implant. This was sufficient volume to ensure that the entire surface of the implant was easily saturated with liquid thus helping to create a uniform deposition of the drug on the implant. This technique resulted in deposit of the ZA solution on and within the entire implant, not just on the superficial region containing HA. The implant was subsequently dried in an oven at 50° C. for 24 hours to ensure fluid evaporation. The result was an implant with some ZA bound chemically to the HA coating and some ZA left on the inner, non HA-coated tantalum struts, presumably unbound and available for more immediate release upon re-exposure to fluid. The implant was weighed before and after the deposition process to verify the amount of retained ZA. The implants were sterilized using ethylene oxide (EtO), however one skilled in the art will appreciate that other know methods of sterilization may also be employed.

Assay of ZA Elution. Assays of ZA in solution were achieved using UV spectrophotometry. Bisphosphonates on their own lack a detectable chromophore, making them difficult to assay by simple conventional analytical methods. However, the metal chelating properties of bisphosphonates are well known. When bisphosphonates complex with certain metal ions, a chromophore with suitable. UV activity for spectrophotometric analysis is created (Ostovic D, Stelmach C, Hulshizer B. Pharmaceutical Research. 10:470-472, 1993). The method for assaying ZA in aqueous-based solutions is based on the formation of a ZA complex with iron (III) ions (Kuljanin J, Jankovic I, Nedeljkovic J, Prstojevic D, Marinkovic V. Journal of Pharmaceutical and Biomedical Analysis. 28:1215-1220, 2002). Of the three components in the prescription drug Zometa™ (ZA, mannitol, and sodium citrate), only ZA forms a complex with iron (III) ions. A standard solution of iron (III) chloride in perchloric acid is added to known concentrations of Zometa™ and the absorbance is measured at 290 nm to create a calibration curve. A highly acidic medium is needed to prevent the hydrolysis of the iron (III) ions. Aliquots of the soak solution from the Zometa™-coated implants can be analyzed by adding the standard iron (III) chloride solution to the soak solution and measuring the absorbance at 290 nm. By measuring the absorbance, the concentration of the sample can be calculated and thus the mass of the drug released from the implant for a given time period can be determined. UV absorbance of aqueous solutions of mannitol and sodium citrate indicated that they do not interfere with ZA absorbance when iron (III) is used as the chelating agent.

Four porous tantalum implants with and without HA coating were deposited with 0.05 mg of ZA as described. For each implant group, elution characteristics were ascertained by immersing each implant in a test tube containing 5 ml of 0.9% saline at 3TC. At mutiple test intervals (1 min, 3 min, 5 min, 10 min, 15 min, 30 min, 1 hr, 6 hrs, 12 hrs, 1 day, 3 days, 7 days, 14 days, 21 days, 42 days, 84 days, and 98 days), the implant was removed from the test tube, the saline was thoroughly mixed, and aliquots were removed for ZA assays using UV spectrophotometry. After each time interval for each implant, the implant was placed in a test tube with fresh replacement of 5 ml of saline. This elution model avoided build up of boundary layers and more closely resembled a dynamic system. The 84-day assay time corresponded to the 12 week length of the in vivo implant studies. Assays ceased once the total amount of ZA was released.

In Vivo Studies. The previously described canine ulnar intramedullary implant model was utilized (study approved by institutional review board) (Bobyn J D, Tanzer M, Harvey EJ, Krygier JJ, Little DG. J Bone Joint Surg (Br), In press, 2005). The surgical procedure involved anesthetizing the dog with a general anesthesia and under sterile conditions exposing the proximal ulna. A two-centimeter incision was made over the olecranon process and the triceps tendon was split by sharp dissection down to bone. Under fluoroscopic guidance, a 5.0 mm drill was oriented along the long axis of the ulna and in line with the intramedullary canal. A 5.5 cm long hole was drilled under fluoroscopy to ensure the proper orientation of the drill hole and to prevent cortical penetration. The porous implant was then tapped down the intramedullary canal of the ulna with a punch and mallet. The implant was slightly countersunk to avoid postoperative irritation of the overlying triceps tendon. The wound was irrigated and closed in a standard fashion. The procedure was repeated on the contralateral side. Positioning of the implants inevitably varied somewhat in terms of depth of insertion within the canal and spatial orientation within the canal. This together with differences in ulna size from animal to animal resulted in variability of the proximity of different regions of each implant to endosteal cortical bone. Each dog received either two control HA coated implants without ZA or two HA coated implants dosed with 0.05 mg ZA. Five control dogs and four with ZA-dosed implants were studied at 12 weeks. This protocol was utilized instead of one with a control and a ZA-dosed implant in each animal because it avoided the possibility of systemic absorption of ZA from one side and influence of a control implant on the other side. No dogs had any complications or systemic illness related to the ZA administration.

Histological examination. After sacrifice, the ulnae were harvested, stripped of soft tissue, radiographed and processed for undecalcified hard-section histology (FIG. 6). This involved dehydration in ascending solutions of ethanol, defatting in ether and acetone, and embedding in methylmethacrylate. Each implant was cut transversely into 6 or 7 sections at 7-8 mm intervals. The sections were radiographed and polished, sputter coated with gold-palladium, and imaged with backscattered scanning electron microscopy. For each section, computerized image analysis based on grey level discrimination was used to identify bone and implant and to generate quantitative information on the extent of bone ingrowth, defined as the percentage of the available porosity that was filled with new bone. Also tabulated in each section was the number and size of the individual islands of bone within the implant pores. In sections cut through the ulnar diaphysis, where delineation of the endosteal cortex was clearly evident, the total area of peri-implant bone contained within the intramedullary canal was also tabulated. In these calculations the implant area (and bone within) was not included. For each section, the peri-implant bone was expressed as a percentage of the total peri-implant area within the intramedullary canal (not including the implant).

Statistical analysis. The quantitative histological data were statistically analyzed using multiple two-level hierarchical models. At the first level of the model, the set of results from the limbs of each dog was assumed to follow a normal distribution with dog-specific means and a global variance parameter. At the second level of the model, the means from each dog in each group (control, ZA-dosed) from the first level followed a second normal distribution, with the mean representing the overall mean for the treatment or control groups and the variance representing the variability within the group. A similar statistical model was also run where the results for each dog were allowed to vary with the distance (section level) along the ulna. As these results were virtually identical to those from the model without this extra variable, only the results from the simple hierarchical model are presented. The mean values and differences between means for control and ZA-dosed implants were estimated with 95% confidence intervals (CI). These data included the amount of peri-implant bone in diaphyseal sections expressed as a percentage of the intramedullary canal size, the overall extent of bone ingrowth, and the number of bone islands within the implant pores and bone island size.

Results

Figure 7:
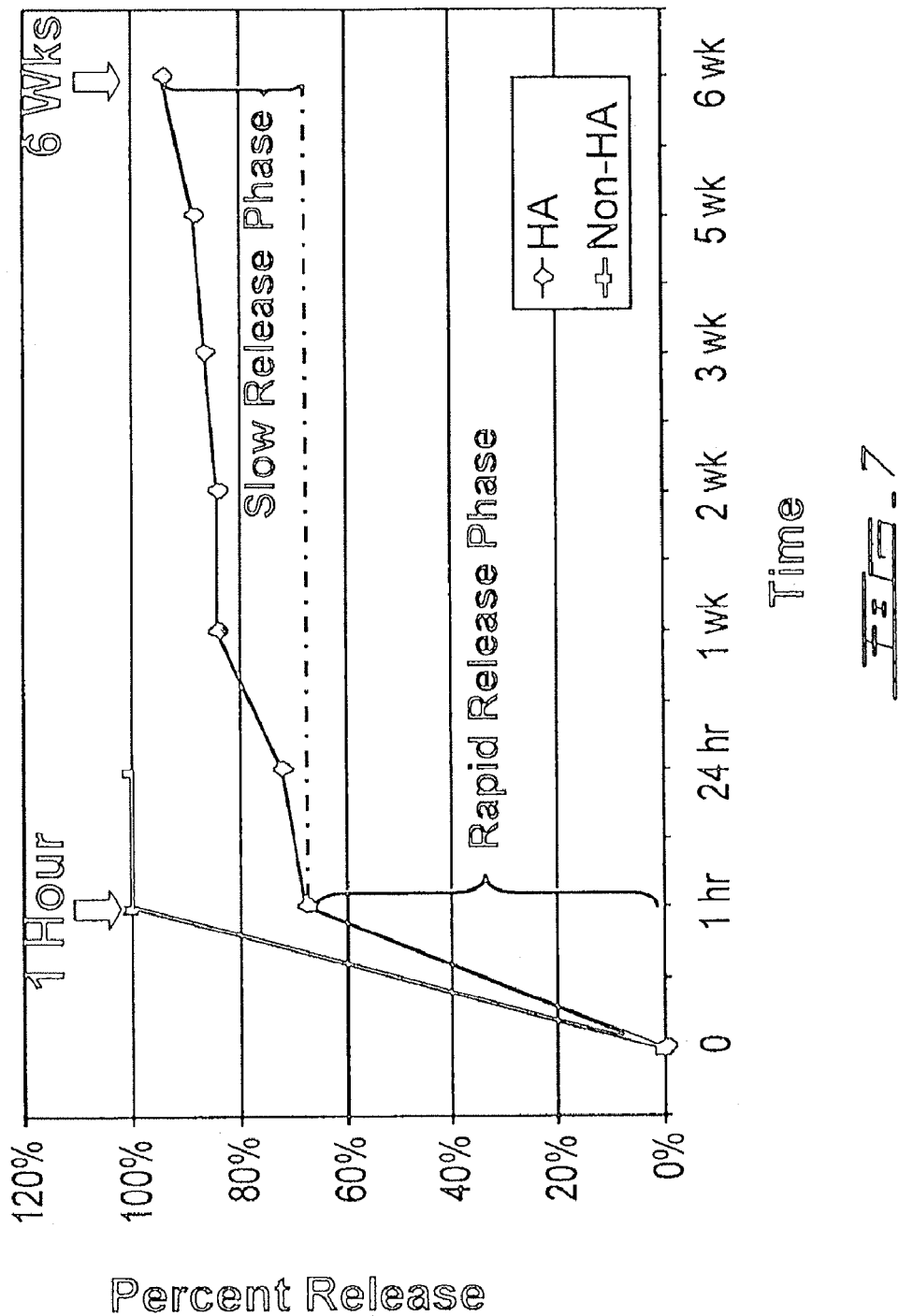
FIG. 7. illustrates elution curves of the percent release in saline of zoledronic acid from non-HA-coated and HA-coated implants dosed with 0.05 mg zoledronic acid. Data points at each time period represent the mean of 4 soaked implants with standard deviation. Note the rapid and complete release of zoledronic acid on implants without HA coating compared to those with HA coating.

ZA Elution. The elution experiment indicated very different release characteristics for implants with and without HA coating as shown in FIG. 7. All of the ZA was released from the non-HA coated implant within 1 hour, confirming that the ZA did not bind to the implant. However, only about 65% of the ZA was released from the HA-coated implant in the same time frame. Almost 95% of the ZA was released from the HA-coated implant after soaking for 6 weeks, confirming slow release of the bound ZA over this time.

Figure 8:
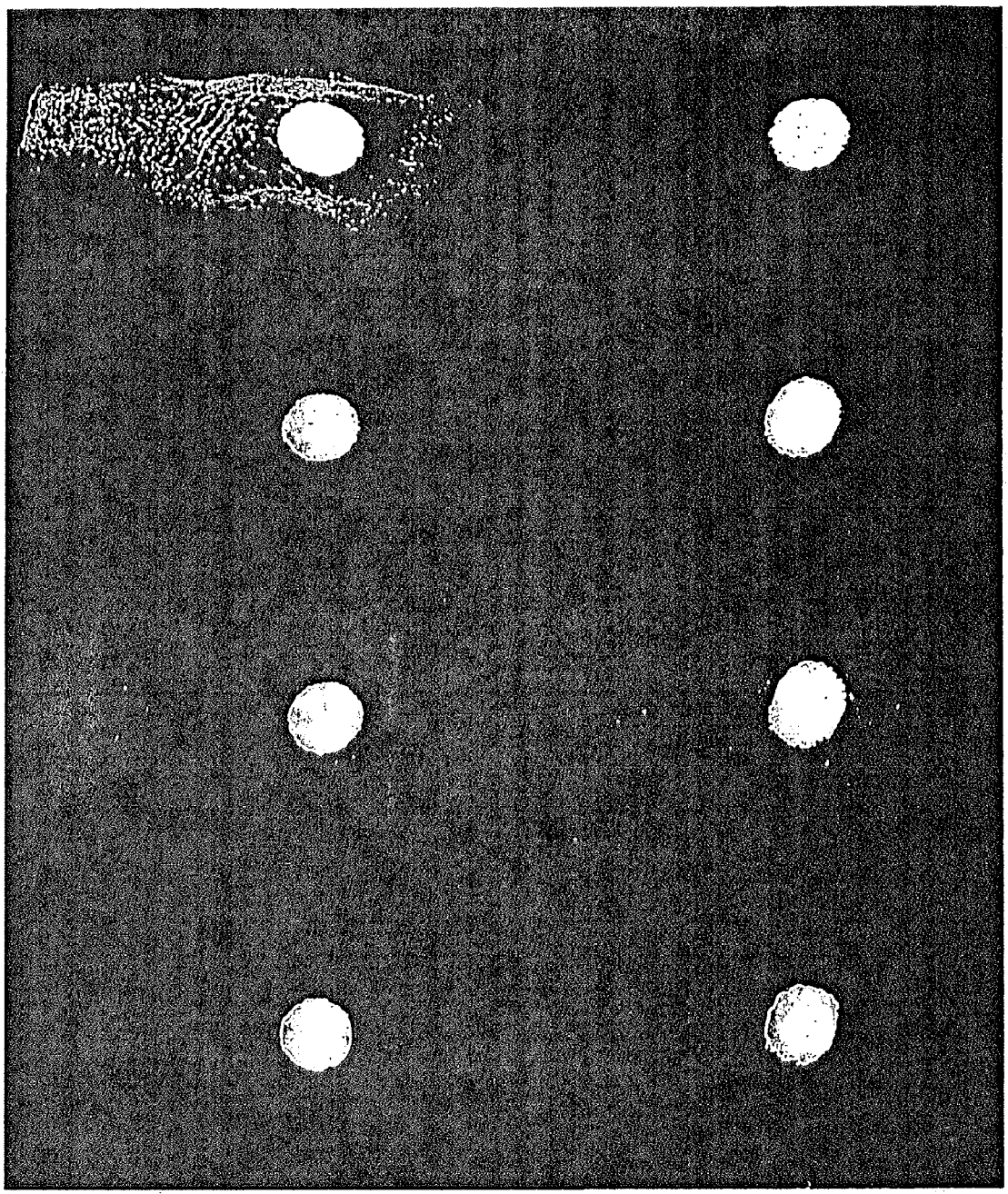
FIG. 8. is a representative contact radiographs of serial transverse histologic sections. Control (left) and ZA-dosed (right) implants are depicted extending from the metaphyseal (top) to diaphyseal (bottom) regions of the ulna. Additional bone and/or greater peri-implant bone density is visible in the ZA-dosed sections compared with controls.

Histoloaic examination. A total of 62 histologic sections from 10 control implants and 54 sections from 8 ZA-dosed implants were examined with contact radiography and backscattered scanning electron microscopy. The contact radiographs revealed varying degrees of peri-implant bone within the intramedullary canal in all sections. This bone was almost always more dense and/or abundant in sections of ZA-dosed implants compared with control implants (FIG. 8). In some sections of the ZA-dosed implants, the peri-implant bone formation was so extensive that the intramedullary canal appeared to be virtually obliterated with bone (FIGS. 9, 10). This was most evident in the metaphyseal and metaphyseal-diaphyseal region of the ulna. However, even the diaphyseal region of the canine ulna, where there is normally fatty tissue and little intramedullary bone, demonstrated bone augmentation around the ZA-dosed implants (FIG. 10). The backscattered scanning electron images revealed the extent of peri-implant bone more clearly; 24 control sections from 4 dogs and 24 ZA-dosed sections from 4 dogs were selected from diaphyseal regions for quantification of peri-implant bone. These data are listed in Table 2. The mean percentage filling of the peri-implant space with bone in control sections was 13.8% (95% CI 2.7 to 24.5) compared with 32.2% (95% CI 21.7 to 43.0) for ZA-dosed sections. The 18.4% difference of the means was significant (95% CI 3.3 to 33.7). In relative terms, there was on average 2.3 times more peri-implant bone around the ZA-dosed implants compared with controls.

TABLE 2

Peri-implant bone relative to intramedullary canal size by dog and overall (%)

| | *Control Dog # | | | | |
| --- | --- | --- | --- | --- | --- |
| | 1 | 2 | 3 | 4 | Mean (95% CI) |
| Bone within Canal | 7.3 | 14.8 | 21.6 | 11.4 | 13.8 (2.7 to 24.5) |
| | †ZA Dog # | | | | |
| | 1 | 2 | 3 | 4 | Mean (95% CI) |
| Bone within Canal | 19.8 | 38.5 | 30.4 | 40.0 | 32.2 (21.7 to 43.0) |

*24 sections, 8 implants
†24 sections, 8 implants
ZA: zoledronic acid
CI = confidence interval New bone formation within the pores of the tantalum implants was observed in all sections, to varying degrees (FIGS. 9, 10, 11). There was a general tendency for more bone ingrowth at the implant periphery than in the center. Although there would tend to be less osteogenic stimulus within the implant center, small islands of bone were observed throughout the implant cross-sections, to varying degrees. The quantitative histologic data on bone ingrowth are listed in Tables 3 and 4 below. The mean extent of bone ingrowth for the 10 control implants was 12.5% (95% CI 9.9 to 15.1), while the mean extent of bone ingrowth for the 8 ZA-dosed implants was 19.8% (95% CI 16.9 to 22.6), a 7.3% difference that was significant (95% CI 3.5 to 11.1) and easily noticed upon visual comparison of control and ZA-dosed sections (FIG. 11). In relative terms, there was on average 58% more net bone growth into ZA-dosed implants compared with controls.

TABLE 3

Mean extent of bone ingrowth by dog and overall (%)

| | *Control Dog # | | | | | |
|---|---|---|---|---|---|---|
| | 1 | 2 | 3 | 4 | 5 | Mean (95% CI) |
| Ingrowth | 13.9 | 11.6 | 10.0 | 12.8 | 14.2 | 12.5 (9.9 to 15.1) |
| | †ZA Dog# | | | | | |
| | 1 | 2 | 3 | 4 | | Mean (95% CI) |
| Ingrowth | 16.0 | 20.3 | 20.3 | 22.6 | | 19.8 (16.9 to 22.6) |

*62 sections, 10 implants
†54 sections, 8 implants
ZA: zoledronic acid
CI = confidence interval

TABLE 4

Mean number and size of bone islands by dog and overall

| | *Control Dog # | | | | | |
|---|---|---|---|---|---|---|
| | 1 | 2 | 3 | 4 | 5 | Mean (95% CI) |
| # Bone Islands | 131 | 121 | 152 | 142 | 131 | 135 (102 to 168) |
| Bone Island Size (mm$^2$) | 0.017 | 0.014 | 0.010 | 0.014 | 0.016 | 0.014 (0.008 to 0.020) |
| | †ZA Dog # | | | | | |
| | 1 | 2 | 3 | 4 | | Mean (95% CI) |
| # Bone Islands | 109 | 155 | 206 | 131 | | 150 (113 to 187) |
| Bone Island Size (mm$^2$) | 0.033 | 0.016 | 0.016 | 0.028 | | 0.023 (0.016 to 0.031) |

*62 sections, 10 implants
†54 sections, 8 implants
ZA: zoledronic acid
CI = confidence interval There was no statistically significant difference in the mean number of bone islands within the implant pores between the control group (mean=135, 95% CI 102 to 168) and the ZA-dosed group (mean=150, 95% CI 113 to 187). However, the bone islands within the implant pores were on average 0.009 mm$^2$ larger in the ZA-dosed implants (95% CI 0.001 to 0.017). The bone islands in the control implants had a mean size of 0.014 mm$^2$ (95% CI 0.007 to 0.021) compared with the ZA-dosed implants which had a mean size of 0.023 mm$^2$ (95% CI 0.016 to 0.030). This represented a 71% relative difference in the size of the bone islands.

Disscussion

This controlled experiment illustrated very clearly that ZA can be effectively delivered directly from an HA coated intramedullary implant. While this was elucidated in the context of ulnar implants, the findings easily extrapolate to any cementless orthopaedic device such as a hip replacement prosthesis. The locally delivered ZA resulted in a net gain in both peri-implant and intra-implant bone formation. Of the two measured regions of net bone formation, the intramedullary canal was much more substantially affected by the ZA-induced alteration of bone remodeling than the pores within the implant. This makes sense in that the normal reparative stimulus to reaming the canal would be strongest at the (mechanically disrupted) endosteal surface of the canal and weakest at the center of the canal, where the implant tended to be located and where there is little native bone. Quantitative measurement of peri-implant bone was confined to histologic sections from the diaphysis, where delineation of the endosteal border was most evident, but the additional bone around ZA-dosed implants, compared with controls, was evident radiographically and histologically in the sections from the metaphysis. However, this could not be quantified because the thin cortices and more extensive cancellous bone of the metaphysis made identification of the intramedullary canal and quantification of peri-implant bone unreliable.

The additional bone with the pores of ZA-dosed implants (mean of 58%) was substantial and could be of value for augmenting mechanical attachment of the implant and enhancing implant survivorship. Only the bone within the more superficial region of the implant pores would be expected to contribute to fixation per se; this was the area where more bone tended to form, possibly influenced by the presence of the HA coating. It is of interest to note that the extent of bone ingrowth in this study was substantially higher than in a previous study using systemically administered ZA, both for control implants and ZA-dosed implants. This is likely due to differences between the studies: 6 additional weeks of implantation, the HA coating, and the local levels of ZA.

This experiment verified the utility of HA for chemically binding the ZA and delaying its elution over time. Although the optimum ZA release rate is an unknown factor, based on our prior study in which systemically injected ZA (fast exposure) caused marked enhancement of bone ingrowth, it seems logical that a faster, as opposed to slower release rate would be effective. Healing and remodeling start immediately after surgery and recruitment of osteoclasts occurs early after surgery when remodeling is most active. In this context it is important to note that ZA binds irreversibly with bone and that once administered the concentration of ZA in bone changes very little over time (Li E C and Davis L E. Clinical Therapeutics 25:2669-2708, 2003). It is also important to note from the work of Peter et al that ZA exposure to a bone surface (i.e., endosteal bone) results in local persistence of the drug; in other words, diffusion from a local site is very low (Peter B, Gauthier O, Guicheux J, Bouler J M, van Lenthe H, Muller R, Zambelli P Y, Pioletti D P: Poster presentation, Trans 7$^{th}$ World Biomat Congress, Sydney, Australia 2004, p 1174). The pilot elution experiment indicated that about 60% of ZA on an HA-coated implant was released very early (analogous to systemic injection), followed by a slower release of the remainder. This appeared to be a reasonable elution characteristic for the purposes of the in vivo studies, although further experimentation in this area is required for optimization.

According to Li and Davis (Li E C and Davis L E. Clinical Therapeutics 25:2669-2708, 2003), at concentrations greater than $2.5 \times 10{-}10$ mol/L ZA can be toxic to bone by inhibiting osteoblast proliferation and DNA synthesis. Peter et al (Peter B, Gauthier O, Guicheux J, Bouler J M, van Lenthe H, Muller R, Zambelli P Y, Pioletti D P: Poster presentation, Trans $7^{th}$ World Biomat Congress, Sydney, Australia 2004, p 1174) recently examined the response of murine (MC3T3) and human (MG-63) osteoblastic cells to ZA and determined that a concentration below 10 μM can be considered safe for cellular activity. Based on these studies it was decided that a ZA dose of 0.05 mg should fall well within the safe range. Based on the release rate of ZA in saline solution, an estimate of the canine ulnar bone volume contained within the peri-implant space, the target local bone concentration described in earlier studies (Li E C and Davis L E. Clinical Therapeutics 25:2669-2708, 2003; Peter B, Gauthier O, Guicheux J, Bouler J M, van Lenthe H, Muller R, Zambelli P Y, Pioletti D P: Poster presentation, Trans $7^{th}$ World Biomat Congress, Sydney, Australia 2004, p 1174) and our earlier ulnar study with systemic ZA (Bobyn J D, Tanzer M, Harvey EJ, Krygier JJ, Little DG. J Bone Joint Surg (Br), In press, 2005.), the 0.05 mg dose was also thought to lie within the biologically effective range. It was clearly sufficient for altering local bone remodeling and causing a net gain in bone formation around and within the porous tantalum implants without any histologic evidence of cellular toxicity. Prior to human application of this drug delivery concept, further studies would have to be performed to clarify the minimum effective dose for eliciting an appreciable gain in net local bone formation. It was of interest to note that the number of bone islands within the pores of control and ZA-dosed implants did not differ significantly; the same occurred with our previous study using systemic ZA at a dose of 0.1 mg/kg (Bobyn J D, Tanzer M, Harvey EJ, Krygier JJ, Little DG. J Bone Joint Surg (Br), In press, 2005). With both studies, the additional bone within porous implants exposed to ZA was primarily due to larger bone island size, not increased number, further supporting the notion that ZA acts by suppressing catabolic remodeling as opposed to boosting anabolic activity.

Although the preferred dose of ZA applied to the implant is about 0.05 mg, more or less bisphosphonate can be used. Particularly, the experiments were conducted using total ZA doses of 0.2 mg and 0.4 mg. While increasing the dosage of ZA was found to produce more bone formation around and within the implant, the additional bone formed was found to be woven bone, i.e. bone which is more immature relative to the bone formed when using a total dose of 0.05 mg. Thus, such higher doses of ZA have shown to promote bone for which the maturity is negatively affected. Accordingly, and perhaps somewhat counter-intuitively, it has been found that the lower ZA dose of 0.05 mg produces the best results of the experiments conducted. A ZA dose of at least less than 0.1 mg is therefore preferred, with a dose of 0.05 mg being the most preferred dose of ZA applied to the implant.

The present bone implant drug delivery system is preferably biocompatible, mechanically strong, capable of achieving adequate drug loading, simple to fabricate, and unaffected by sterilization. With a porous implant there is the additional consideration that the drug delivery system does not occlude the pores or hinder bone ingrowth. In the cardiac stent industry bioresorbable polymers are utilized, however, with a bioresorbable polymer delivery system there exists the need to identify the chemical degradation products of the polymer and their effects on local tissue response. The specific use of HA as an immobilizer of ZA on an orthopaedic implant is not the only possible means to provide modulated, multi-phasic release of a bone stimulating active agent to local bone surround the implant, however the preferred embodiment described above is simple, effective, and advantageous given the long clinical history of HA use in hip implant design. The concept proposed does not necessarily require use of a porous implant. HA may also be used as an adjuvant fixation on implants without porous surface treatments and would be equally effective for binding ZA in these instances. The reason for the rapid release of 60% of the ZA was most likely due to its presence (availability) on the inner, non-HA coated regions of the porous tantalum struts.

Therefore conventional orthopaedic implants can be effectively used to locally deliver pharmaceutical agents to bone for modulation of bone healing/formation. The net positive remodeling response to a locally eluted bisphosphonate was consistent and substantial, to an extent that could provide clinical benefit to implant stability and fixation. A significant advantage of bisphosphonates over bone morphogenetic proteins is their relatively low cost, an important consideration given the increasingly stringent global health care constraints. An ancillary benefit of using bisphosphonates is their documented effect on mitigating the effects of stress shielding and wear particle induced osteolysis (Shanbhag A S, Hasselman C T, Rubash H E. Clin Orthop 344:33-43, 1997; Soininvaara T A, Jurvelin J S, Miettinen H J A, Suomalainen O T, Alhava E M, Kroger P J. Calcified Tissue Int 71:472-477, 2002; Venesmaa P K, Kroger H P, Miettinen H J, Jurvelin J S, Suomalainen O T, Alhava E M. J Bone Miner Res 16:2126-2131, 2001; Wilkinson J M, Stockley I, Peel N F, Hamer A J, Elson R A, Barrington N A, Eastell R. J Bone Miner Res 16:556-564, 2001). This concept has wide ranging implications for various types of bone devices, arthroplasty implants being the most obvious but also for fracture fixation, tumor resection, limb lengthening implants, spinal implant, and/or dental implants.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An implantation method for releasing an active agent in at least two phases, the method comprising the steps of:
   providing an implant having a porous portion;
   coating the porous portion with a calcium phosphate compound;
   contacting the implant with a bisphosphonate compound to form: (i) a bisphosphonate layer chemically bound to the calcium phosphate compound at the surface of the porous portion, and (ii) bisphosphonate molecules non-chemically attached inside pores of the porous portion;
   implanting the implant at least partially within a subject;
   burst-releasing, in a first release phase, the non-chemically attached bisphosphonate molecules in the subject upon contact with body fluids of the subject; and slowly releasing, in a second release phase, the chemically bound bisphosphonate layer in the subject upon contact with the body fluids.

2. The method of claim 1, wherein the release of the non-chemically attached bisphosphonate molecules and the chemically bound bisphosphonate layer in the subject promotes bone formation around or within the implant; and
wherein the promoted bone formation is modulated by the first and second release phases.

3. The method of claim 1, wherein the implant is at least one of a joint implant, a spine implant and a dental implant.

4. The method of claim 3, wherein the joint implant is one of a hip, knee, elbow, ankle and shoulder implant.

5. The method of claim 1, wherein the porous portion comprises a biocompatible surface having interconnecting pores formed therein.

6. The method of claim 5, wherein the biocompatible surface is selected from the group consisting of a sintered bead porous surface, a fiber metal porous surface, a textured surface and a plasma spray surface.

7. The method of claim 1, wherein the implant is fabricated from a material comprising at least one of titanium, titanium-based alloy, zirconium, niobium, cobalt-based alloy, tantalum, stainless steel and polymer.

8. The method of claim 1, wherein the pores are of a size ranging from 20 to 1000 μm.

9. The method of claim 1, wherein the pores are of an average size of 100 to 700 μm.

10. The method of claim 1, wherein the bisphosphonate is a bisphosphonate of at least a third generation.

11. The method of claim 10, wherein the bisphosphonate is selected from the group consisting of bisphosphonate zoledronic acid (ZA), ibandronate and risedronate.

12. The method of claim 11, wherein the bisphosphonate is bisphosphonate zoledronic acid provided on the implant in a dose of less than 0.4 mg.

13. The method of claim 12, wherein a dose of less than 0.05 mg of the bisphosphonate zoledronic acid is provided on the implant.

14. The method of claim 10, wherein the bisphosphonate is provided on the implant in a maximum dose equivalent to a bisphosphonate zoledronic acid dose of about 0.4 mg.

15. The method of claim 14, wherein the maximum dose is equivalent to a bisphosphonate dose of about 0.05 mg.

16. The method of claim 1, wherein the calcium phosphate compound comprises at least one of hydroxyapatite, tricalcium phosphate, dicalcium phosphate, amorphous calcium phosphate, and tetracalcium phosphate monoxide.

17. The method of claim 1, wherein the bisphosphonate includes nitrogen.

18. A bone implantation method for releasing an active agent in at least two phases, the method comprising the steps of:
providing a bone implant having a porous portion;
coating an outer surface of the porous portion with a calcium phosphate compound;
applying a bisphosphonate compound to the porous portion to form: (i) a bisphosphonate layer chemically bound to the calcium phosphate compound on the outer surface of the porous portion, and (ii) bisphosphonate compound molecules non-chemically attached to the porous portion within pores thereof free of the calcium phosphate compound;
implanting the implant at least partially within a subject;
releasing, in a first release phase, the non-chemically attached bisphosphonate molecules from the implant to promote bone formation around or within the implant;
releasing, in a second release phase, the chemically bound bisphosphonate layer from the implant to promote bone formation around or within the implant; and
wherein the release rate of the first release phase is different from the release rate of the second release phase.

19. The method of claim 18, wherein the promoted bone formation is Modulated by the first and second release phases.

20. The method of claim 18, wherein the implant is at least one of a joint implant, a spine implant and a dental implant.

21. The method of claim 20, wherein the joint implant is one of a hip, knee, elbow, ankle and shoulder implant.

22. The method of claim 18, wherein the porous portion comprises a biocompatible surface having interconnecting pores formed therein.

23. The method of claim 22, wherein the biocompatible surface is selected from the group consisting of a sintered bead porous surface, a fiber metal porous surface, a textured surface and a plasma spray surface.

24. The method of claim 18, wherein the implant is fabricated from a material comprising at least one of titanium, titanium-based alloy, zirconium, niobium, cobalt-based alloy, tantalum, stainless steel and polymer.

25. The method of claim 18, wherein the pores are of a size ranging from 20 to 1000 μm.

26. The method of claim 18, wherein the pores are of an average size of 100 to 700 μm.

27. The method of claim 18, wherein the bisphosphonate is a bisphosphonate of at least a third generation.

28. The method of claim 27, wherein the bisphosphonate is selected from the group consisting of bisphosphonate zoledronic acid (ZA), ibandronate and risedronate.

29. The method of claim 28, wherein the bisphosphonate is bisphosphonate zoledronic acid provided on the implant in a dose of less than 0.4 mg.

30. The method of claim 29, wherein a dose of less than 0.05 mg of the bisphosphonate zoledronic acid is provided on the implant.

31. The method of claim 27, wherein the bisphosphonate is provided on the implant in a maximum dose equivalent to a bisphosphonate zoledronic acid dose of about 0.4 mg.

32. The method of claim 31, wherein the maximum dose is equivalent to a bisphosphonate dose of about 0.05 mg.

33. The method of claim 18, wherein the calcium phosphate compound comprises at least one of hydroxyapatite, tricalcium phosphate, dicalcium phosphate, amorphous calcium phosphate, and tetracalcium phosphate monoxide.

34. The method of claim 18, wherein the chemically bound bisphosphonate layer is slowly released in the subject and the non-chemically attached bisphosphonate molecules are released more quickly in the subject.

35. The method of claim 18, wherein the bisphosphonate includes nitrogen.

36. A bone implantation method for releasing an active agent, the method comprising the steps of:
providing a biocompatible bone implant;
selectively coating the bone implant with a calcium phosphate compound to form: (i) at least a first porous region with a calcium phosphate coating thereon, and (ii) at least a second region free of the calcium phosphate;
applying a bisphosphonate compound to the bone implant to form: (i) a bisphosphonate layer chemically bound to the calcium phosphate coating of the first region, and (ii) bisphosphonate molecules non-chemically attached to the second region of the bone implant;
implanting the implant at least partially within a subject;
releasing the bisphosphonate from the first and second regions at different rates after implanting the implant.

37. The method of claim 36, wherein the non-chemically attached bisphosphonate molecules are released in the subject at a rate greater than that of the chemically bound bisphosphonate layer.

38. The method of claim 36, wherein the release of the non-chemically attached bisphosphonate molecules and the chemically bound bisphosphonate layer in the subject promotes bone formation around or within the implant; and
 wherein the promoted bone formation is modulated by the different release rates of the bisphosphonate in the subject.

39. A bone implantation method for releasing a material in at least two phases, the method comprising the steps of:
 providing a biocompatible bone implant;
 applying a binding agent to the bone implant to form: (i) at least a first region with applied binding agent, and (ii) at least a second region free of the binding agent;
 applying a bone growth stimulating active agent to the bone implant to form: (i) an active agent layer chemically bound to the applied binding agent of the first region, and (ii) active agent molecules non-chemically attached to the second region of the bone implant;
 implanting the implant at least partially within a subject;
 rapidly releasing, in a first release phase, the non-chemically attached active agent molecules of the second region to bone of the subject proximate the implant to locally promote bone formation around or within the implant;
 gradually releasing, in a second release phase, the chemically bound active agent layer of the first region to bone of the subject proximate the implant to locally promote bone formation around or within the implant;
 wherein the bone implant includes a porous portion and has an outer surface defining the first region and internal pores defining the second region
 wherein the release rate of the first release phase is different from the release rate of the second release phase; and
 wherein the promoted bone formation is modulated by the first and second release phases;
 wherein the active agent is a bisphosphonate and the binding agent is a calcium phosphate compound.

40. The method of claim 39, wherein the bisphosphonate is at least a third generation bisphosphonate.

41. The method of claim 39, wherein the calcium phosphate compound comprises at least one of hydroxyapatite, tricalcium phosphate, dicalcium phosphate, amorphous calcium phosphate, and tetracalcium phosphate monoxide.

* * * * *